US010806642B2

(12) United States Patent
Tagomori et al.

(10) Patent No.: US 10,806,642 B2
(45) Date of Patent: Oct. 20, 2020

(54) ABSORBENT ARTICLE WITH A CONCAVE GROOVE

(71) Applicant: DAIO PAPER CORPORATION, Ehime (JP)

(72) Inventors: Junta Tagomori, Tochigi (JP); Yasushi Otani, Tokyo (JP)

(73) Assignee: DAIO PAPER CORPORATION, Ehime (JP)

( * ) Notice: Subject to any disclaimer, the term of this patent is extended or adjusted under 35 U.S.C. 154(b) by 867 days.

(21) Appl. No.: 15/505,738

(22) PCT Filed: Aug. 20, 2015

(86) PCT No.: PCT/JP2015/073375
§ 371 (c)(1),
(2) Date: Feb. 22, 2017

(87) PCT Pub. No.: WO2016/031668
PCT Pub. Date: Mar. 3, 2016

(65) Prior Publication Data
US 2017/0246056 A1    Aug. 31, 2017

(30) Foreign Application Priority Data

Aug. 29, 2014   (JP) .................................. 2014-175221
Aug. 29, 2014   (JP) .................................. 2014-175966

(51) Int. Cl.
*A61F 13/15*      (2006.01)
*A61F 13/20*      (2006.01)
(Continued)

(52) U.S. Cl.
CPC ...... *A61F 13/533* (2013.01); *A61F 13/15707* (2013.01); *A61F 13/4753* (2013.01);
(Continued)

(58) Field of Classification Search
CPC .......... A61F 13/15707; A61F 13/47272; A61F 13/4753; A61F 13/4756; A61F 13/51108;
(Continued)

(56) References Cited

U.S. PATENT DOCUMENTS 4,678,464 A     7/1987  Holtman
4,795,455 A  *  1/1989  Luceri .................... A61F 13/474
                                                            604/386

(Continued)

FOREIGN PATENT DOCUMENTS

JP     S59-207150      11/1984
JP     2001-137286     5/2001
(Continued)

OTHER PUBLICATIONS

International Search Report dated Nov. 17, 2015.
Japanese Office Action dated Apr. 27, 2016.

*Primary Examiner* — Michele M Kidwell
(74) *Attorney, Agent, or Firm* — IPUSA, LLC

(57) ABSTRACT

A absorbent article has a concave groove that satisfies (1) a relationship between a depth "h" of a bottom surface portion of the concave groove, and a distance "S" from a bottom end "G" of the concave groove to an upper end "K" from which a concavity of the concave groove starts is 1.5h<S, (2) a relationship between a width "b" of a bottom surface of the concave groove, and a width "B" of a liquid collection area expressed by a distance between the upper ends "K" and "K" at both sides of the concave groove is B≥3b, and (3) a relationship between a dimension "a" of a square concave groove expressed by a product of the width "b" of the bottom surface and the depth "h" of the bottom surface, and a cross-sectional dimension "A" of the concave groove is A≥2a.

8 Claims, 12 Drawing Sheets

(51) Int. Cl.
  *A61F 13/533* (2006.01)
  *A61F 13/511* (2006.01)
  *A61F 13/472* (2006.01)
  *A61F 13/475* (2006.01)
  *A61F 13/536* (2006.01)
  *A61F 13/551* (2006.01)
  *A61F 13/56* (2006.01)
  *A61F 13/51* (2006.01)
  *A61F 13/45* (2006.01)
  *A61F 13/53* (2006.01)

(52) U.S. Cl.
  CPC .... *A61F 13/4756* (2013.01); *A61F 13/47272* (2013.01); *A61F 13/51108* (2013.01); *A61F 13/536* (2013.01); *A61F 13/5514* (2013.01); *A61F 13/5611* (2013.01); A61F 2013/16 (2013.01); A61F 2013/4587 (2013.01); A61F 2013/51078 (2013.01); A61F 2013/530007 (2013.01); A61F 2013/530481 (2013.01)

(58) Field of Classification Search
  CPC .. A61F 13/533; A61F 13/536; A61F 13/5514; A61F 2013/4587; A61F 2013/51078; A61F 13/51104; A61F 13/5611; A61F 2013/53007
  See application file for complete search history.

(56) References Cited

U.S. PATENT DOCUMENTS

| | | | |
|---|---|---|---|
| 5,795,345 A * | 8/1998 | Mizutani | A61F 13/4756 604/380 |
| 6,498,283 B1 | 12/2002 | Wada et al. | |
| 6,563,013 B1 * | 5/2003 | Murota | A61F 13/4704 604/379 |
| 8,998,871 B2 * | 4/2015 | Kuroda | A61F 13/15707 604/385.16 |
| 9,040,769 B2 * | 5/2015 | Kurihara | A61F 13/4756 604/380 |
| 10,071,000 B2 * | 9/2018 | Umemoto | A61F 13/51108 |
| 10,166,152 B2 * | 1/2019 | Suzuki | A61F 13/4756 |
| 10,342,716 B2 * | 7/2019 | Tagomori | A61F 13/4704 |
| 10,555,843 B2 * | 2/2020 | Suzuki | A61F 13/4751 |
| 2007/0073253 A1 | 3/2007 | Miyama et al. | |
| 2008/0183150 A1 * | 7/2008 | Nanjyo | A61F 13/4756 604/385.101 |
| 2012/0265162 A1 * | 10/2012 | Kuramochi | A61F 13/4758 604/385.101 |
| 2013/0165889 A1 | 6/2013 | Kawakami | |

FOREIGN PATENT DOCUMENTS

| | | |
|---|---|---|
| JP | 2001-509716 | 7/2001 |
| JP | 2002-531172 | 9/2002 |
| JP | 2003-506150 | 2/2003 |
| JP | 2007-082956 | 4/2007 |
| JP | 2008-173247 | 7/2008 |
| JP | 2009-112590 | 5/2009 |
| JP | 2010-110535 | 5/2010 |
| JP | 2012-050542 | 3/2012 |
| JP | 2012-096079 | 5/2012 |
| WO | 98/31320 | 7/1998 |
| WO | 00/32145 | 6/2000 |
| WO | 01/10372 | 2/2001 |

* cited by examiner

ABSORBENT ARTICLE WITH A CONCAVE GROOVE

BACKGROUND OF THE INVENTION

1. Field of the Invention

The present invention mainly relates to an absorbent article used in incontinence pads, disposal diapers and the like, and an absorbent article provided with at least a concave groove for introducing urine therein formed at a skin side surface along a longitudinal direction.

2. Description of the Related Art

In conventional absorbent articles, an absorbent body is provided between a liquid impermeable backsheet such as a polyethylene sheet or a non-woven fabric made of laminated polyethylene sheets, and a liquid permeable topsheet such as a non-woven fabric or a permeable plastic sheet.

This kind of absorbent article has been improved many times, and in particular, various products in which a concave groove is formed at a front surface along a longitudinal direction are provided, as one of a temporary storing means and urine diffusing means, for receiving a large amount of urine expelling at once at a small area and diffusing it rapidly, such as incontinence pads.

For example, Patent Document 1 discloses an absorbent article that includes a front surface sheet constituting a skin contacting surface, a backsheet constituting a non-skin contacting surface, and an absorbent layer provided between the both sheets. In the absorbent layer, an upper absorbent layer and a lower absorbent layer having different dimensions are stacked, and a step is formed. A concave portion that extends in a longitudinal direction of the absorbent article is integrally formed in the front surface sheet and the absorbent layer.

Further, Patent Document 2 discloses an absorbent article that includes an upper absorbent body at a skin contacting surface and a lower absorbent body at a non-skin contacting surface. A middle high portion formed by the upper absorbent body and the lower absorbent body is provided with a concavity, formed at the skin contacting surface, that extends in a longitudinal direction. The concavity is an open portion penetrating the upper absorbent body, and the lower absorbent body is positioned at a lower surface of the upper absorbent body such that to constitute a bottom surface of the open portion.

Meanwhile, an absorbent article is known in which an absorbent body is provided between a liquid impermeable backsheet such as a polyethylene sheet or a non-woven fabric made of laminated polyethylene sheets, and a liquid permeable topsheet such as a non-woven fabric or a liquid permeable plastic sheet. Side flaps at which the absorbent body does not exist are formed at both sides of the absorbent body, and gathers are formed by providing elastic stretchable members at the side flaps along a longitudinal direction.

As such an absorbent article, for example, Patent Document 3 discloses an absorbent pad that includes a backsheet layer, a liquid permeable upper surface sheet layer stacked on the backsheet layer, an absorbent assembly sandwiched between the backsheet layer and the topsheet layer, and side flaps disposed transversely outward of the absorbent assembly, each of the side flaps including an elastic member that is at least partially positioned outside of a planer surface of the absorbent assembly when the absorbent pad is at a substantially flat status. The absorbent pad is formed to have a rigidity larger than a predetermined rigidity.

Patent Document 1: Japanese Laid-open Patent Publication No. 2008-173247

Patent Document 2: Japanese Laid-open Patent Publication No. 2009-112590

Patent Document 3: Japanese Translation of PCT International Application Publication No. JP-T-2003-506150

As the concave portion formed in the absorbent article disclosed in Patent Document 1 or 2 is formed along a longitudinal direction with a relatively narrow width, although a large effect of diffusion and absorption of urine can be obtained when the amount of urine is small, if a large amount of urine is expelled at once, urine volume flowing in the concave portion is small and there is a risk that side leak occurs while the urine transfers a front surface. Further, as the concave portion is formed with a narrow width, if the absorbent article shifts laterally a bit when being worn, the concave portion is shifted from an expelling area of a body and urine is not expelled directly in the concave portion. Then, the urine is expelled outside the concave portion. As a result, the urine diffuses toward a center side direction and an outer side direction. Then, the urine that flows toward the outer side directions may leak from the side.

Meanwhile, the absorbent pad of Patent Document 3 is formed to have a large rigidity. Thus, when the absorbent pad is item packaged by being folded in three in a longitudinal direction at bend lines extending in a width direction, strong creases are formed at the bend lines under the item packaged status. Thus, when the absorbent article is taken out from the item packaging, the absorbent article is formed to have a U-shape or the like as a whole as front and rear sides with respect to the bend lines, respectively, stand toward a skin side by the creases. Further, when gathers are formed by providing elastic stretchable members at both sides of the absorbent article, the front and rear sides with respect to the bend lines, respectively, may stand toward the skin side due to retraction force of the elastic stretchable members.

Here, it is considered that the concave groove extending along the longitudinal direction is provided at the skin side, as disclosed in Patent Document 1 or 2, of such an absorbent article in which the front and rear sides with respect to the bend lines, respectively, stand toward the skin side as described above. In such a case, if the concave groove is provided such that its front end and rear end are positioned at a center side with respect to the bend lines, respectively, in other words, the concave groove is provided in the middle of the front and rear bend lines, when the urine temporarily reserved in the concave groove reaches the front end or the rear end of the concave groove, the urine tends to be accumulated at the front end or the rear end and overflowed, and the overflowed urine easily diffuses in the width direction along the creases to cause side leak. Further, in such a case, the front end and the rear end of the concave groove tend to be positioned near the bend lines, respectively. Thus, as the absorbent body is compressed due to the folding of the absorbent article, and the depth of the concave groove may be shallow, this is also a factor of overflowing of the urine from the front end or the rear end.

Further, for the absorbent article in which the concave groove is formed along the longitudinal direction, the rigidity at the concave groove portion is extremely low. Thus, the concave groove is easily collapsed due to pressure of legs from both sides in the width direction or the like when the absorbent article is worn. At this time, if a slip stopper adhesive layer provided at an outer surface of the liquid impermeable backsheet for stopping slip between an underwear when being worn is positioned at an area that overlaps the concave groove in the thickness direction, there is a problem that the slip stopper adhesive layer adheres with each other and the concave groove that is collapsed is easily retained at such a status.

Thus, a first problem to be solved by the present invention is to provide an absorbent article including an absorbent body provided between a liquid permeable topsheet and a backsheet, and at least a single concave groove for flowing urine therein formed at a skin side surface along a longitudinal direction, capable of controlling a flowing direction of expelled urine so as to flow along a concave groove side even when the absorbent article is laterally shifted while being worn, and capable of causing the absorbent body to absorb the urine rapidly without causing side leak by enlarging the reserving volume of the concave groove.

Further, a second problem to be solved is to prevent the urine temporarily reserved in the concave groove from overflowing from an end portion of the concave groove to cause side leak. Further, a problem to be solved is to provide an absorbent article in which a slip stopper adhesive layer does not adhere with each other even when the concave groove is collapsed.

SUMMARY OF THE INVENTION

As the invention of claim 1 to solve the above problem, there is provided an absorbent article including: an absorbent body provided between a liquid permeable topsheet and a backsheet; and at least a single concave groove for flowing urine therein formed at a skin side surface along a longitudinal direction, wherein a transverse plane shape of the concave groove satisfies following conditional expressions (1) to (3), (1) a relationship between a depth "h" of a bottom surface portion of the concave groove, and a distance "S" from a bottom end "G" of the concave groove to an upper end "K" from which a concavity of the concave groove starts is 1.5 h<S, (2) a relationship between a width "b" of a bottom surface of the concave groove, and a width "B" of a liquid collection area expressed by a distance between the upper ends "K" and "K" at both sides of the concave groove is B≥3b, and (3) a relationship between a dimension "a" of a square concave groove expressed by a product of the width "b" of the bottom surface of the concave groove and the depth "h" of the bottom surface portion, and a cross-sectional dimension "A" of the concave groove is A≥2a.

Further, there is provided an absorbent article, wherein in the concave groove, a density "ρ1" of the absorbent body at the bottom is greater than or equal to 1.5 times of a density "ρ2" of the absorbent body at a peripheral general portion which is not compressed.

The invention of claim 1 has a feature in a transverse plane shape of the concave groove. Specifically, the transverse plane shape of the concave groove satisfies the conditional expressions (1) to (3).

First, the first conditional expression (1) defines an affection area of the concave groove in a transverse plane direction, in other words, the width "B" of the liquid collection area designed for the expelled urine to flow toward the bottom side of the concave groove, by the relationship with the depth "h" of the concave groove. Specifically, when the relationship between the depth "h" of the bottom surface portion of the concave groove, and the distance "S" from the bottom end "G" of the concave groove to the upper end "K" from which the concavity of the concave groove starts is 1.5 h<S, the width "B" of the liquid collection area becomes 2S+b. Thus, even when the absorbent article is laterally shifted when being worn, as long as the urine expelling area of the body is positioned within the width "B" of the liquid collection area, the flowing direction of the expelled urine can be controlled to flow along the concave groove toward the bottom side.

Next, similarly, the second conditional expression (2) defines the width "B" of the liquid collection area by the relationship with the width "b" of the bottom surface of the concave groove. Specifically, when the relationship between the width "b" of the bottom surface of the concave groove, and the width "B" of the liquid collection area expressed by a distance between the upper ends "K" and "K" at both sides of the concave groove is B≥3b, a sufficient width for the width "B" of the liquid collection area can be ensured. Thus, even when the absorbent article is laterally shifted when being worn, the flowing direction of the expelled urine can be controlled to flow along the concave groove side.

Further, the third conditional expression (3) defines the cross-sectional dimension "A" of the concave groove by the relationship with the cross-sectional reserving dimension "a" where the concave groove is formed by a rectangular shape. Specifically, when the relationship between the dimension "a" of the square concave groove expressed by a product of the width "b" of the bottom surface of the concave groove and the depth "h" of the bottom surface portion, and the cross-sectional dimension "A" of the concave groove is A≥2a, a sufficient reserving volume for the concave groove can be ensured. Thus, even when the large amount of the urine is expelled at once, the urine can be temporarily reserved in the concave groove once, and thereafter, the urine can be absorbed rapidly in the absorbent body.

According to the invention, in the concave groove, a density "ρ1" of the absorbent body at the bottom is greater than or equal to 1.5 times of a density "ρ2" of the absorbent body at a peripheral general portion which is not compressed. Thus, as the density of the absorbent body at the bottom is higher than that of other portions, the urine can be rapidly flowed toward the bottom of the concave groove to be absorbed in the absorbent body.

As the invention of claim 2, there is provided the absorbent article according to claim 1, wherein the absorbent body is provided with an absorbent body concave portion formed at a surface at a liquid permeable topsheet side along a longitudinal direction of the absorbent body over a range including an urine expelling area in the longitudinal direction, without compression, and the concave groove is formed by embossing from a front surface side of the liquid permeable topsheet, under a status that the liquid permeable topsheet is stacked, to a bottom surface of the absorbent body concave portion, and wherein, before embossing, a fabric weight per unit area "β1" of the absorbent body at the bottom of the concave groove is less than or equal to 55% of a fabric weight per unit area "β2" of the absorbent body at the general portion which is not compressed.

According to the above invention of claim 2, the absorbent body is previously provided with an absorbent body concave portion, without compression, and the concave groove is formed by embossing from a front surface side of the liquid permeable topsheet, under a status that the liquid permeable topsheet is stacked on the absorbent body concave portion, to a bottom surface of the absorbent body concave portion, and wherein, before embossing, a fabric weight per unit area "β1" of the absorbent body at the bottom of the concave groove is less than or equal to 55% of a fabric weight per unit area "β2" of the absorbent body at the general portion which is not compressed. Compared with a case in which a concave portion is formed by compressing the absorbent body so that the polymer or the pulp at the bottom becomes high density, the bulge of the bottom when absorbing the urine is extremely small for the above described absorbent body concave portion and the status of the concave groove can be retained after absorbing the urine.

As the invention of claim 3, there is provided the absorbent article according to claim 1 or 2, further including standing gathers at both side portions at a skin surface side, wherein the width "B" of the liquid collection area is greater than or equal to ⅓ of an inside size "W" of standing ends of the standing gathers.

According to the above invention of claim 3, the width "B" of the liquid collection area is defined by the relationship with the inside size "W" of the standing ends of the standing gathers. Specifically, the width "B" of the liquid collection area is set to be greater than or equal to ⅓ of the inside size "W" of the standing ends of the standing gathers. By forming the width "B" of the liquid collection area to be greater than or equal to ⅓ of the inside size "W" of the standing ends of the standing gathers, which is a width capable of absorbing the urine, large amount of the expelled urine can be effectively flowed into the concave groove and can be absorbed in the absorbent body.

As the invention of claim 4, there is provided the absorbent article according to claim 1 or 2, wherein a length of the concave groove in a longitudinal direction is 100 to 180 mm, and the width "b" of the bottom surface of the concave groove is 5 to 30 mm.

According to the above invention of claim 4, the length of the concave groove in the longitudinal direction and the width of the bottom surface are defined. Specifically, it is preferable that the length of the concave groove in the longitudinal direction is 100 to 180 mm, and the width "b" of the bottom surface of the concave groove is 5 to 30 mm.

As the invention of claim 5, there is provided the absorbent article according to claim 1, wherein the absorbent article is folded in three in a longitudinal direction by front and rear bend lines, and a front side and a rear side with respect to the front and rear bend lines, respectively, stand toward a skin side when the absorbent article is taken out from an item packaging, and wherein a front end of the concave groove extends toward the front side of the front bend line, a rear end of the concave groove extends toward the rear side of the rear bend line, or the front end of the concave groove extends toward the front side of the front bend line and the rear end of the concave groove extends toward the rear side of the rear bend line.

According to the above invention of claim 5, an absorbent article which is formed to have a U-shape or the like as a whole as front and rear sides with respect to the bend lines, respectively, stand toward a skin side by the creases when the absorbent article is taken out from the item packaging in which the absorbent article is folded in three. As such, the reason that the rear side and the front side stand toward the skin side from the bend lines, respectively, may be a case due to creases formed because the fabric weight per unit area of the pulp of the absorbent body is high, a case due to retraction force of the elastic stretchable members that constitute the gathers BS provided at the both side portions of the absorbent article, or the like.

In such an absorbent article, the concave groove is formed at a range that extends toward a front side or a rear side, or both of the sides with respect to the bend lines for item packaging the absorbent article, respectively. With this, when the urine temporarily reserved in the concave groove flows toward the end portions of the concave groove, the front and rear sides with respect to the bend lines, respectively, that stand toward the skin side become walls and function as parapets to return the urine flowed to the end portion sides. Thus, the urine does not overflow from the concave groove, and the urine is accumulated in the concave groove to be gradually absorbed and retained in the absorbent body. Thus, the urine temporarily reserved in the concave groove is prevented from flowing out from the concave groove to cause side leak.

As the invention of claim 6, there is provided the absorbent article according to claim 5, wherein a fabric weight per unit area of pulp of the absorbent body at a portion other than the concave groove is greater than or equal to 400 g/m$^2$, and wherein a ratio, with respect to a weight of the absorbent body, which is a total of a weight of entire pulp and a weight of entire polymer, of the weight of the entire pulp is greater than or equal to 55%.

According to the above invention of claim 6, the absorbent body whose fabric weight per unit area is relatively high and whose pulp amount is high is used such as the fabric weight per unit area of pulp of the absorbent body at a portion other than the concave groove is greater than or equal to 400 g/m$^2$, and the ratio of the weight of the pulp with respect to the weight of the absorbent body is greater than or equal to 55%. In such a case, if the absorbent article is folded at the bend lines of the width direction in the longitudinal direction, the front and rear sides with respect to the bend lines tend to stand toward the skin side by the creases. However, according to the absorbent article of the invention, overflowing of the urine from the end portions of the concave groove can be prevented by the above described structure, and the absorbent body is easily bent because the concave groove functions as a flexible axis when being worn, the gathers formed at side flaps at both sides can easily adhere to the skin surface.

As the invention of claim 7, there is provided the absorbent article according to claim 5, further including a slip stopper adhesive layer provided at an outer surface side of the backsheet, and wherein the slip stopper adhesive layer is not provided at a range that overlaps the concave groove in a thickness direction.

According to the above invention of claim 7, as the slip stopper adhesive layer is not provided at a range that overlaps the concave groove in the thickness direction, even when the concave groove is collapsed in the width direction when being worn, the slip stopper adhesive layer is prevented from adhering with each other because a space is formed.

As the invention of claim 8, there is provided the absorbent article according to claim 5, wherein the concave groove is provided with one of or both of a wide width portion whose groove width is enlarged and a deep depth portion whose groove depth is increased at an end portion that extends outward with respect to the bend line, and the wide width portion or the deep depth portion is formed from a center side position to the end portion with respect to the bend line.

According to the above invention of claim 8, for the absorbent article in which the end portions of the concave groove extend outward with respect to the bend lines, respectively, there is a problem that, when the urine that flows along the concave groove strongly collides against the wall portions standing toward the skin side, the urine overflows from both sides of the concave groove, diffuses both sides along the bend lines and side leak occurs. In order to solve such a problem, means to lower the flowing speed before the urine that flows along the concave groove collides against the wall portions by increasing the cross-sectional dimension of the concave groove is provided. Specifically, one of or both of the wide width portion and the deep depth portion is provided at end portions of the concave groove that extend outward with respect to the bend lines, respectively. With this, before colliding against the wall portion that stands toward the skin side, the flowing speed is decreased as the cross-sectional dimension of the concave groove increases and the urine does not overpass the concave groove. Further, as the dimension around the concave groove increases at the wide width portion and the deep depth portion, absorbing dimension of the urine is increased and absorbing ability for the urine is improved.

As described above in detail, according to the invention, it is possible to control a flowing direction of expelled urine so as to flow along a concave groove side even when the absorbent article is laterally shifted while being worn, and to cause the absorbent body to absorb the urine rapidly without causing side leak by enlarging the reserving volume of the concave groove.

Further, the urine temporarily reserved in the concave groove can be prevented from overflowing from an end portion of the concave groove to cause side leak. Further, an absorbent article in which a slip stopper adhesive layer does not adhere with each other even when the concave groove is collapsed can be provided.

DETAILED DESCRIPTION OF THE PREFERRED EMBODIMENTS

Next, embodiments (incontinence pad) of the present invention will be described below with reference to drawings.

(Basic Structure of Incontinence Pad 1)

Figure 1:
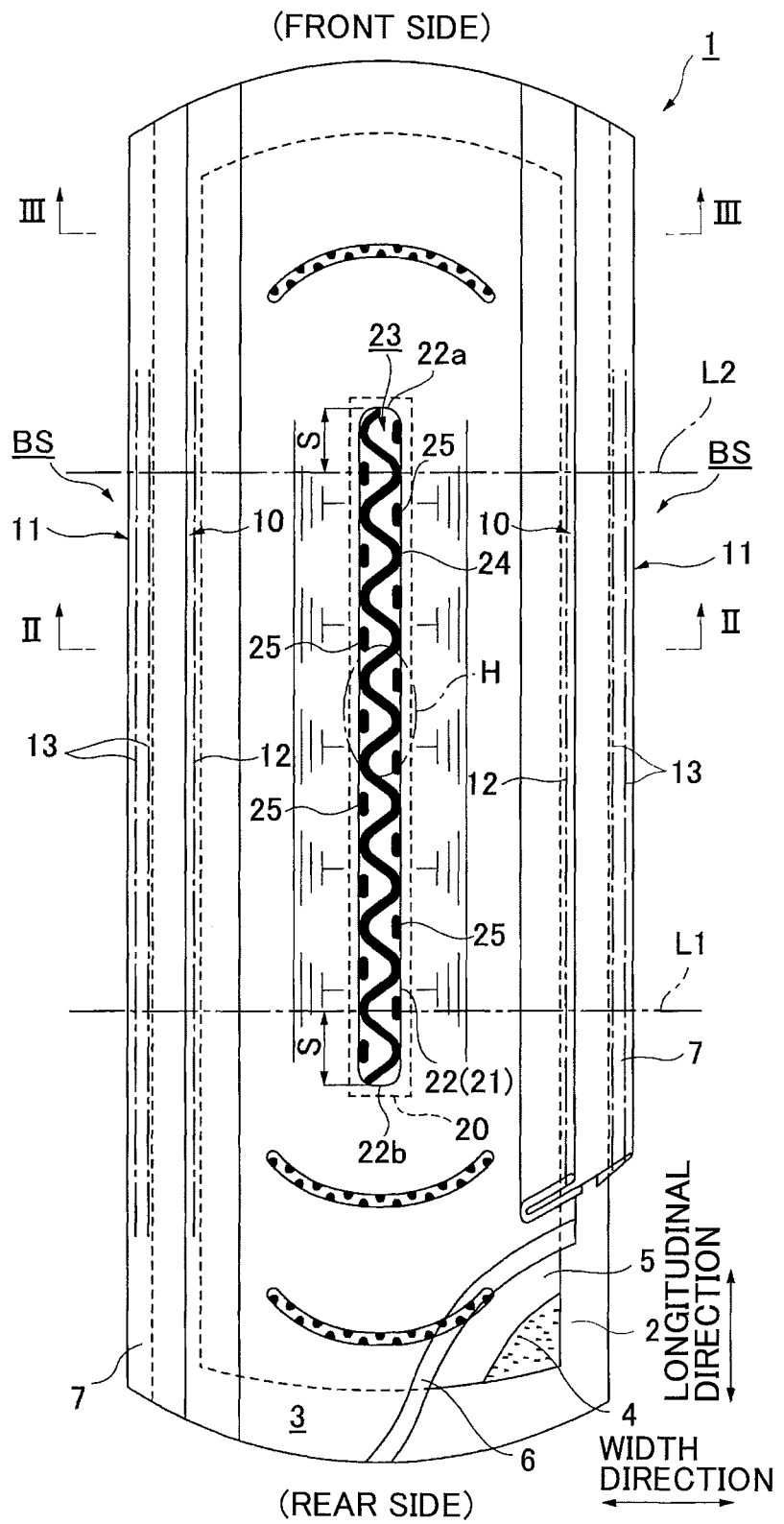
FIG. 1 is a partially broken developed view of an incontinence pad 1 of the invention.
Figure 2:
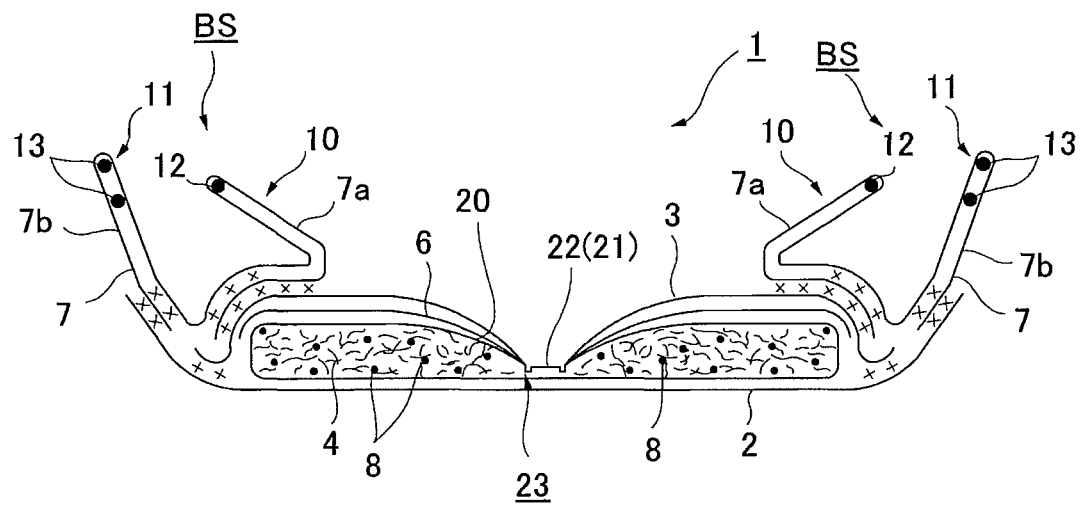
FIG. 2 is a cross-sectional view taken along a II-II line of FIG. 1.
Figure 3:
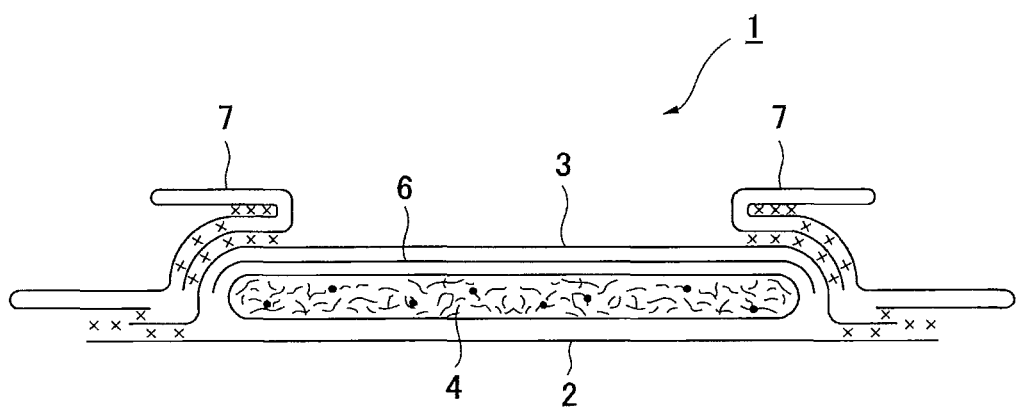
FIG. 3 is a cross-sectional view taken along a III-III line of FIG. 1.

As illustrated in FIG. 1 through FIG. 3, an incontinence pad 1 of the present invention is mainly constituted of a liquid impermeable backsheet 2 made of polyethylene, a liquid permeable topsheet 3 that allows urine and the like to rapidly permeate, an absorbent body 4 made of cotton-like pulp, synthetic pulp, or the like, and that is provided between both the sheets 2 and 3, an encapsulating sheet 5 such as a crepe paper sheet, a non-woven fabric or the like that surrounds the absorbent body to retain a shape and to improve diffusivity of the absorbent body 4, a hydrophilic second sheet 6 disposed between the liquid permeable topsheet 3 and the absorbent body 4, as necessary, and side non-woven fabrics 7 forming a matched pair of standing gathers BS that protrude toward a skin side in a predetermined zone including at least a urine expelling area H in the longitudinal direction, while standing from approximately side edge parts of the absorbent body 4. Around the absorbent body 4, the outer end portions of the liquid impermeable backsheet 2 and the liquid permeable topsheet 3 are bonded with an adhesive such as a hot-melt adhesive or an adhesive means such as a heat seal and the like at end portions in the longitudinal direction, and the liquid impermeable backsheet 2 laterally protruding from the absorbent body 4 and the side non-woven fabrics 7 are bonded with the adhesive such as the hot-melt adhesive or the adhesive means such as the heat seal and the like at the edge portions on both sides.

Hereinafter, the structure of the incontinence pad 1 is further described in more detail. A sheet material having at least water shielding properties such as polyethylene, polypropylene or the like is used in the liquid impermeable backsheet 2. In addition to this, a non-woven fabric sheet can be also used after ensuring substantial impermeability by providing a waterproof film to cover the non-woven fabric sheet (in this case, the liquid impermeable backsheet is composed of the waterproof film and the non-woven fabric sheet). In recent years, a material having moisture permeability is often preferably used to prevent sweating. A microporous sheet obtained by forming a sheet by melting and kneading inorganic filler in olefin series resin such as polyethylene and polypropylene and then extruding the sheet in one axial direction or two axial directions, is preferably used as the waterproof and moisture permeable sheet material.

A perforated or imperforate non-woven fabric or a porous plastic sheet is preferably used as the liquid permeable topsheet 3. For example, a regenerated fiber such as rayon and cupra, and a natural fiber such as cotton, can be used as a material fiber forming the non-woven fabric in addition to a synthetic fiber including an olefin series such as polyethylene and polypropylene, a polyester series, a polyamide series and the like. As the non-woven fabric, a non-woven fabric obtained by a proper processing method such as a spun lace method, a spun bond method, a thermal bond method, a melt blown method, and a needle punch method, can be used. Among the processing methods, the spun lace method is superior in terms of great flexibility and drape properties, and the thermal bond method is superior in terms of bulkiness and softness.

The absorbent body 4 is, for example, constituted of an absorbable fiber such as a fluff pulp and superabsorbent polymers 8, and is formed into an approximately oval shape extending long in a longitudinal direction of the pad in a planar shape in the illustrated example. The superabsorbent polymers 8 are, for example, formed into granular powders, and are diffused and mixed into the pulp forming the absorbent body 4.

Chemical pulp obtained from wood, a cellulose fiber such as dissolving pulp, and an artificial cellulose fiber such as rayon and acetate, are cited as examples available for the pulp, and softwood pulp having a fiber length longer than that of hardwood pulp is preferably used in terms of function and price. In the incontinence pad 1, as the absorbent body 4 is surrounded by the encapsulating sheet 5, as a result, the encapsulating sheet is provided between the liquid permeable topsheet 3 and the absorbent body 4. Thus, the encapsulating sheet having excellent absorbability serves to rapidly distribute the urine and to prevent urine and the like from flowing back. The fabric weight per unit area of the pulp (general portion (β2) that is not compressed) may be 100 g/m$^2$ to 600 g/m$^2$, and preferably, may be 400 g/m$^2$ to 500 g/m$^2$. It is preferable that the fabric weight per unit area is relatively high compared with a normal panty liner type. Further, it is preferable to use one whose ratio of a weight of pulp is relatively high such as one whose ratio, with respect to a weight of the absorbent body, which is a total of a weight of the entire pulp of the absorbent body 4 and a weight of entire polymer of the absorbent body 4, of the weight of the entire pulp is greater than or equal to 55%, and preferably 60% to 80%.

The fabric weight per unit area is measured by cutting a size of 20 mm×40 mm (±2 mm) from a sample by a roller cutter, measuring the weight and converting the weight to the weight per 1 m$^2$. Further, the weight of the pulp and the weight of the polymer are measured by extracting only pulp fiber or polymer from the absorbent body 4, and measuring each of weights by a meter. Further, the thickness is measured by using a thickness gauge (PEACOCK, dial thickness gauge large type, J-B (measurement range 0 to 35 mm)) manufactured by OZAKI MFG. CO., LTD. while the sample and the thickness gauge are horizontally placed.

For example, a cross-linking polyacrylate, a self-cross-linking polyacrylate, a saponified substance of a cross-linking copolymer of acrylic acid ester and vinyl acetate, a cross-linking substance of a copolymer of isobutylene and maleic anhydride, a cross-linking polysulfonate, and a partially cross-linking substance of a water swellable polymer such as polyethylene oxide and polyacrylamide are cited as examples of the superabsorbent polymer 8. Among the examples, a substance of acryl acid or an acrylate-based substance having a large amount of water absorption and a high absorption speed is preferable. The water-absorbency (water-absorbing ratio) and the water absorption speed of the superabsorbent polymer having the above-mentioned water absorption performance can be adjusted by adjusting the cross-linking density and the cross-linking density gradient in its manufacturing process. The fabric weight per unit area of the polymer is preferably set in a range of 150 g/m$^2$ to 500 g/m$^2$, and further preferably set in a range of 200 g/m$^2$ to 450 g/m$^2$.

Moreover, a synthetic fiber may be mixed into the absorbent body 4. For example, a polyolefin series such as polyethylene or polypropylene, a polyester series such as polyethylene terephthalate and polybutylene terephthalate, and a polyamide series such as nylon, and a copolymer thereof, or a mixture of two kinds thereof, can be used as the synthetic fiber. Furthermore, a composite fiber such as a core-clad type fiber including a core made of a fiber with a high melting point and a clad made of a fiber with a low melting point, a side-by-side type fiber, and a division type, can be also used. When the synthetic fiber is made of a hydrophobic fiber, it is preferable to treat a surface of the synthetic fiber with a hydrophilic agent so as to have hydrophilic properties to the urine.

A paper material such as a tissue or the like, or a liquid permeable sheet such as a non-woven fabric or the like may be used as the encapsulating sheet 5. In particular, it is preferable to use the non-woven fabric for which damage (split) to a material hardly occurs. For such a non-woven fabric, a non-woven fabric processed by a spun bond method or an SMS method, a non-woven fabric processed by a method by which a web is directly formed in a spinning process such as a spun bond method or a melt blow method from an elastic fiber made of thermoplastic elastomer resin or the like, a non-woven fabric containing a material having elasticity such as latex, urethane, olefin based fiber as a main constituent, is preferable as it has a good balance between the thin thickness and the strength. Here, for the encapsulating sheet 5, as long as a surface at a skin contacting surface (front surface) of the absorbent body 4 is not water repellency, its hydrophilic degree is not specifically limited.

The second sheet 6 just has to have hydrophilic properties to the urine. More specifically, a hydrophilic material that has hydrophilic properties in itself can be used as the second sheet 6 by using the regenerated fiber such as rayon and cupra, and the natural fiber such as cotton. Otherwise, a fiber treated to have the hydrophilic properties by treating a surface of a synthetic fiber including an olefin series such as polyethylene and polypropylene, a polyester series, a polyamide series and the like with a hydrophilic agent, can be used. In addition, the second sheet 6 may include a porous film layer on its back side (the absorbent body 4) to provide tension, may be a stacked layer sheet with the encapsulating sheet, and further may be made of a material including pulp.

On both sides of the front surface side of the present incontinence pad 1, side non-woven fabrics 7 are respectively provided along the longitudinal direction over the entire length of the incontinence pad 1, and outer parts of the side non-woven fabrics 7 extend laterally while the liquid impermeable backsheet 2 extends laterally. Side flaps are formed by attaching the laterally extended side non-woven fabric 7 parts to the laterally extended liquid impermeable backsheet 2 parts with the hot-melt adhesive and the like.

Either water-repellent non-woven fabric or hydrophilic non-woven fabric is used as the side non-woven fabric 7 depending on the desired function. For example, when regarding a function of preventing urine and the like from permeating or of improving a texture as important, it is preferable to use the water-repellent non-woven fabric such as SSMS, SMS or SMMS coated with water-repellent agent and the like of a silicon series, a paraffin series and an alkyl chromic chloride series. When regarding the absorbability of the urine as important, it is preferable to use a hydrophilic non-woven fabric obtained by making a swellable or porous synthetic fiber by a method of polymerizing the synthetic fiber in the presence of a compound having a hydrophilic group, for example, an oxidation product of polyethylene glycol, in the manufacture of the synthetic fiber, or a method of treating the surface with a metallic salt such as stannic chloride to partially dissolve the surface to form a porous surface and then to precipitate a metallic hydroxide on the surface, and then providing the hydrophilic property for the synthetic fiber by using capillary action. A fiber obtained by processing the natural fiber, the synthetic fiber or the regenerated fiber by a proper processing method is available for the side non-woven fabric 7.

The side non-woven fabrics 7 are properly folded to form the standing gathers BS of a double structure including the matched pair of inner standing gathers 10, 10 standing from the neighborhood of the edges of the absorbent body 4 toward the skin side, and the matched pair of outer standing gathers 11 that are located outside the inner standing gathers 10, constituted of the liquid impermeable backsheet 2 extending laterally so as to protrude from the absorbent body 4 and the side non-woven fabrics 7, and formed so as to stand toward the skin side. Here, the standing gather BS may have a single gather structure constituted of only one of the inner standing gather 10 or the outer standing gather 11, or may not be formed into a standing gather shape standing toward the skin side by just providing the side non-woven fabric 7 without raising it.

The structure of the inner standing gather 10 and the outer standing gather 11 is described below in more detail. As illustrated in FIG. 2, double sheet parts 7a, 7b are respectively formed on the inner side and the outer side in the width direction by folding both sides of the side non-woven fabric 7 in the width direction. At least one, in the illustrative example, one threadlike elastic stretchable member 12 is fixed at both ends or proper locations in the longitudinal direction, and is provided inside the double sheet part 7a. At least one, in the illustrative example, two threadlike elastic stretchable members 13, 13 are fixed at both ends or proper locations in the longitudinal direction, and are provided inside the double sheet part 7b. By attaching the base edge portion of the double sheet part 7a on the inner side in the width direction to the upper surface of the liquid permeable topsheet 3 provided on a side portion of the absorbent body 4 with a hot-melt adhesive or the like, and attaching the base edge portion of the double sheet part 7b on the outer side in the width direction to the side edge portion of the liquid impermeable backsheet 2 laterally protruding from the absorbent body 4 with the hot-melt adhesive, the inner standing gather 10 standing toward the skin side is formed of the double sheet part 7a on the inner side in the width direction, and the outer standing gather 11 standing toward the skin side is formed of the double sheet part 7b on the outer side in the width direction. Here, as illustrated in FIG. 3, the side non-woven fabric 7 does not include the threadlike elastic stretchable members 12, 13 at the end portions in the longitudinal direction, and the double sheet part 7a on the inner side in the width direction is attached to the absorbent body 4 with a hot-melt adhesive.

(Concave Groove 22)

In the incontinence pad 1 of the embodiment, a single concave groove 22 for flowing urine therein is formed at a front surface side (skin surface side) along a longitudinal direction. The concave groove 22 is provided to receive urine expelled at the front surface of the liquid permeable topsheet 3, temporarily reserve the urine, induce the urine to diffuse in front and rear directions, increase the absorbing speed of the urine in the absorbent body 4 and prevent side leak.

The concave groove 22 may be formed by integrally compressing constituent members from the liquid permeable topsheet 3 to the absorbent body 4, from the front surface of the liquid permeable topsheet 3. However, it is preferable that the concave groove 22 is formed by previously forming an absorbent body concave portion 20 in the absorbent body 4, and providing an emboss portion 21 that compresses constituent members above the absorbent body 4 by compressing along the absorbent body concave portion 20, from the front surface of the liquid permeable topsheet 3 (skin surface side), because deformation of the concave groove 22 due to the pressure of legs can be prevented.

Figure 4:
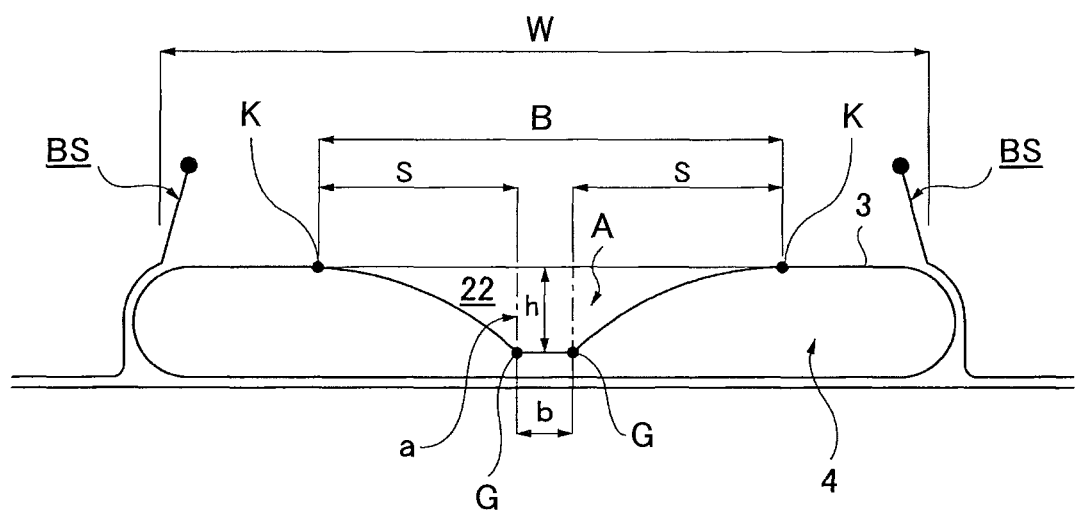
FIG. 4 is a transverse plane view schematically illustrating a transverse plane shape of a concave groove 22.
Figure 5:
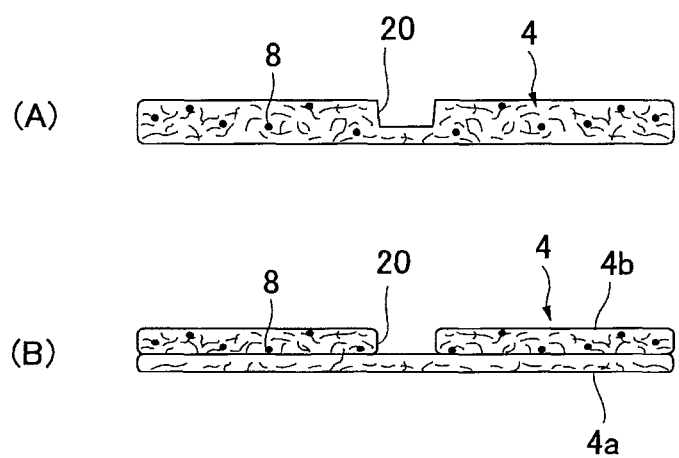
FIG. 5 is a cross-sectional view of an absorbent body 4.

The absorbent body concave portion 20, as a concave groove or a slit, as the concave groove for the illustrated example, is formed in the absorbent body 4 without compression before forming the emboss portion 21. As illustrated in FIG. 4, for example, the absorbent body concave portion 20 is formed by (A) fiber stacking, (B) a staked structure of a lower absorbent body 4a formed by a thickness of a bottom portion of the absorbent body concave portion 20, and an upper absorbent body 4b provided with an opening at a portion corresponding to the absorbent body concave portion 20, or the like, without using compression.

As illustrated in FIG. 1, it is preferable that one absorbent body concave portion 20 is formed at the absorbent body 4 at a center portion in the pad width direction and also at a middle portion in the longitudinal direction corresponding to the urine expelling area H. Alternatively, the absorbent body concave portion 20 may be formed in various embodiments (see FIG. 17 to FIG. 19) such as a plurality of the absorbent body concave portions 20 may be formed with spaces therebetween in the width direction of the incontinence pad 1. Here, when the plurality of absorbent body concave portions 20 are formed, it is preferable that the embossed portion 21 is formed for each of the absorbent body concave portions 20.

The plane size of the absorbent body concave portion 20 may have a length of 100 to 180 mm in the longitudinal direction of the pad, and may have a groove width of 5 to 30 mm (a groove width at a bottom surface). When the concave groove 22 is formed after previously providing the absorbent body concave portion 20, it is preferable that the depth of the absorbent body concave portion 20, before providing the emboss portion 21, is greater than or equal to 45% of the thickness of the absorbent body 4 at a general portion, specifically, about 5 to 8 mm.

The fabric weight per unit area "β1" (not containing polymer) of the absorbent body 4 at the bottom of the absorbent body concave portion 20 (a portion at a liquid impermeable backsheet 2 side, a portion at a non-skin side), before providing the emboss portion 21, may be 70 g/m$^2$ to 280 g/m$^2$, preferably, may be 90 g/m$^2$ to 260 g/m$^2$, and may be less than or equal to 55%, preferably, 40 to 55%, of the fabric weight per unit area "β2" (not containing polymer) of the absorbent body at the general portion which is not compressed. Further, the fabric weight per unit area of the portion of the absorbent polymer 8 may be 0 g/m$^2$ to 270 g/m$^2$, and preferably, may be 0 g/m$^2$ to 35 g/m$^2$.

When providing the emboss portion 21, its plane size may be larger than the size of the absorbent body concave portion 20, or may be smaller than the size of the absorbent body concave portion 20. The highly compressed portion 23, which is further compressed deeper than a bottom surface of the surrounding concave groove 22, with a predetermined pattern is provided at a bottom surface of the emboss portion 21. The pattern of the highly compressed portion 23 is described later.

(Transverse Plane Shape of Concave Groove 22)

According to the incontinence pad 1 of the embodiment, the transverse plane shape of the concave groove 22 is configured to control a flowing direction of expelled urine so as to flow along a concave groove 22 side even when the incontinence pad 1 is laterally shifted while being worn by enlarging a range that promotes flowing in to the concave groove 22, and to cause the absorbent body 4 to absorb the urine rapidly without causing side leak by enlarging the reserving volume of the concave groove 22.

Specifically, with reference to the transverse plane view (lateral cross-sectional view) illustrated in FIG. 4, the transverse plane shape of the concave groove 22 satisfies the following conditional expressions (1) to (3).

(1) A relationship between a depth "h" of a bottom surface portion of the concave groove 22, and a distance "S" from a bottom end "G" of the concave groove 22 to an upper end "K" from which a concavity of the concave groove 22 starts is 1.5 h<S (first conditional expression).

(2) A relationship between a width "b" of a bottom surface of the concave groove 22, and a width "B" of a liquid collection area expressed by a distance between the upper ends "K" and "K" at both sides of the concave groove 22 is B>3b (second conditional expression).

(3) A relationship between a dimension "a" of a square concave groove expressed by a product of the width "b" of the bottom surface of the concave groove 22 and the depth "h" of the bottom surface portion, and a cross-sectional dimension "A" of the concave groove 22 is A≥2a (third conditional expression).

The first conditional expression (1) defines an affection area of the concave groove 22 in a transverse plane direction, in other words, the width "B" of the liquid collection area designed for the expelled urine to flow toward the bottom side of the concave groove 22, by the relationship with the depth "h" of the concave groove 22. Many of concave portions for urine to be flowed therein of conventional absorbent articles are formed with a relatively narrow width. Thus, if a large amount of urine is expelled at once, urine volume flowing in the concave portion is small and there is a risk that side leak occurs while the urine transfers a front surface. Further, as the concave portion is formed with a narrow width, there is a risk that if the absorbent article shifts laterally a bit when being worn, the concave portion is shifted from an expelling area of a body and urine is not expelled directly in the concave portion. However, according to the incontinence pad 1 of the embodiment, the concave groove 22 is formed such that the width of its upper opening is expanded largely in a width direction. Specifically, when the relationship between the depth "h" of the bottom surface portion of the concave groove 22, and the distance "S" from the bottom end "G" of the concave groove 22 to the upper end "K" from which the concavity of the concave groove 22 starts is 1.5 h<S, preferably, is 2 h<S, the width "B" of the liquid collection area becomes 2S+b. Thus, even when the incontinence pad 1 is laterally shifted when being worn, as long as the urine expelling area of the body is positioned within the width "B" of the liquid collection area, the flowing direction of the expelled urine can be controlled to flow along the concave groove 22 toward the bottom side. The depth "h" of the bottom surface portion of the concave groove 22 (the depth to a portion other than the highly compressed portion 23) may be 3 to 20 mm, preferably, may be 7 to 9 mm.

Here, the bottom end "G" of the concave groove 22 to the upper end "K" from which the concavity of the concave groove 22 starts may be an arc-shaped inclined surface that slightly protrudes outwardly (as illustrated) or an linear inclined surface.

The second conditional expression (2) defines the width "B" of the liquid collection area by the relationship with the width "b" of the bottom surface of the concave groove. If only with the first conditional expression (1), the sufficient width "B" of the liquid collection area cannot be ensured when the depth "h" is small. Thus, in addition to the first conditional expression (1), the size of the width "B" of the liquid collection area is defined by the second conditional expression (2). Specifically, when the relationship between the width "b" of the bottom surface of the concave groove 22, and the width "B" of the liquid collection area expressed by a distance between the upper ends "K" and "K" at both sides of the concave groove 22 is B≥3b, preferably, B≥4b, a sufficient width for the width "B" of the liquid collection area can be ensured. Thus, even when the incontinence pad 1 is laterally shifted when being worn, as long as the urine expelling area of the body is positioned within the width "B" of the liquid collection area, the flowing direction of the expelled urine can be controlled to flow along the concave groove 22 toward the bottom side. As described above, it is preferable that the width "b" of the bottom surface of the concave groove 22 is 5 to 30 mm, and more preferably, 10 to 20 mm.

In order to hold the urine in the concave groove 22 even when the large amount of the urine is expelled at once, the third conditional expression (3) defines the cross-sectional dimension "A" of the concave groove 22 by the relationship with the cross-sectional reserving dimension "a" where the concave groove 22 is formed by a rectangular shape. Specifically, when the relationship between the dimension "a" of the square concave groove expressed by a product of the width "b" of the bottom surface of the concave groove 22 and the depth "h" of the bottom surface portion, and the cross-sectional dimension "A" of the concave groove 22 is A≥2a, a sufficient reserving volume for the concave groove 22 can be ensured. Thus, even when the large amount of the urine is expelled at once, the urine can be temporarily reserved in the concave groove 22 once, and thereafter, the urine can be diffused rapidly to be absorbed in the absorbent body 4.

Further, in order to rapidly flow the urine to the bottom side of the concave groove 22, in the concave groove 22, a density "$\rho 1$" (not containing polymer) of the absorbent body at the bottom is greater than or equal to 1.5 times, preferably, greater than or equal to 1.7 times, of a density "$\rho 2$" (not containing polymer) of the absorbent body at a peripheral general portion which is not compressed. Such a relative difference in density of the absorbent body may be provided by the formation of the emboss portion 21 to the bottom of the concave groove 22 or the formation of the highly compressed portion 23, which will be explained later. By providing such a difference in density of the absorbent body, the urine can be rapidly flowed toward the bottom of the concave groove 22 to be absorbed in the absorbent body 4. The density "$\rho 1$" of the absorbent body at the bottom of the concave groove 22 may be 0.060 to 0.150 g/cm$^3$, preferably, may be 0.070 to 0.140 g/cm$^3$. The density "$\rho 2$" of the absorbent body at the general portion may be 0.020 to 0.070 g/cm$^3$, preferably, may be 0.030 to 0.060 g/cm$^3$.

Further, it is preferable that the width "B" of the liquid collection area is greater than or equal to ⅓, preferably, ½ of an inside size "W" of standing ends of the standing gathers BS. By forming the width "B" of the liquid collection area to be greater than or equal to ⅓ of the inside size "W" of the standing ends of the standing gathers BS, which is a width capable of absorbing the urine, large amount of the expelled urine can be effectively flowed into the concave groove 22 and can be absorbed in the absorbent body 4.

(Highly Compressed Portion 23 of Concave Groove 22)

Figure 6:
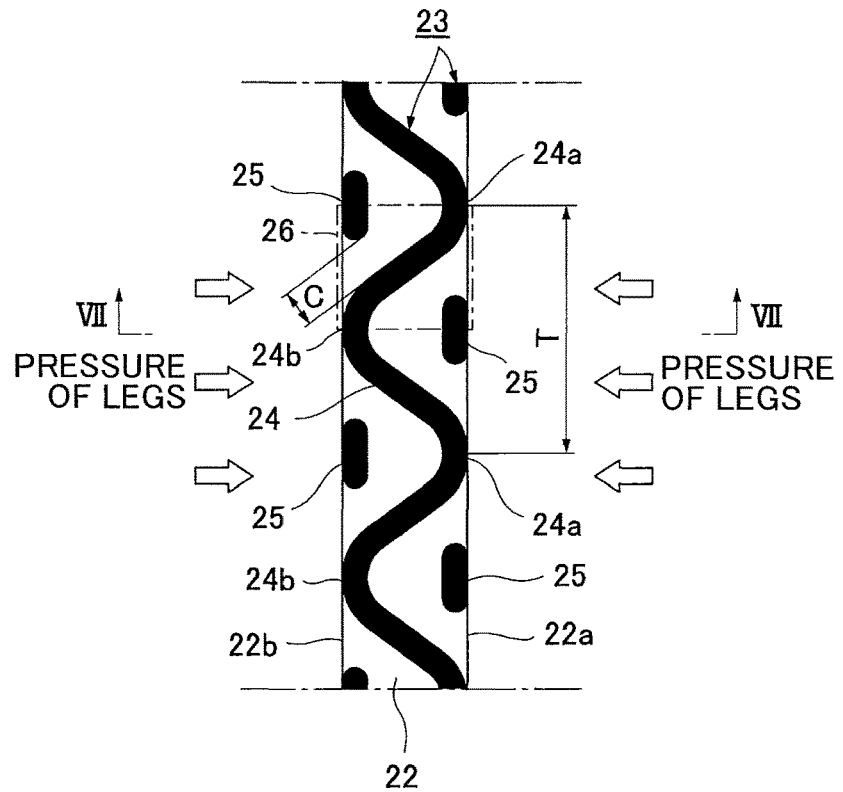
FIG. 6 is an enlarged plan view of the concave groove 22.

Hereinafter, the highly compressed portion 23 is described. The highly compressed portion 23 is a portion that is further compressed to be deeper than a bottom surface of the surrounding concave groove 22, and is formed at the bottom surface of the concave groove 22 with a predetermined pattern. Specifically, as illustrated in FIG. 6, the highly compressed portion 23 is constituted by a wavy-shaped first emboss 24 and a second emboss 25. The wavy-shaped first emboss 24 is formed by a pattern in which a unit section 26, obtained by sectioning the concave groove 22 in a longitudinal direction, is repeatedly positively inverted in a longitudinal direction of the groove, the wavy-shaped first emboss 24 being formed by extending in the width direction of the groove while inclining in the longitudinal direction of the groove to cross from a side end at one side to a side end at the other side of the concave groove 22 in the unit section, in a planar view. The wavy-shaped first emboss 24 is formed by a pattern that extends along the concave groove 22 in total, and that concaves and protrudes repeatedly at both sides in the width direction such that to reciprocate between the both side edges of the concave groove 22. The second emboss 25 is formed along the concave groove 22 at a side edge portion of the concave groove 22, that is opposite of each of protruding portions 24a and 24b of the wavy-shaped first emboss 24 that protrude outwardly in the width direction, respectively.

The wavy-shaped first emboss 24 is a continuous line formed in a wave shape such as a wavy-shaped curved line, a zig-zag line (see FIG. 9) or the like that reciprocates between one side edge 22a and the other side edge 22b of the concave groove 22. In the wavy-shaped first emboss 24, the protruding portion 24a that protrudes toward the one side edge 22a and the protruding portion 24b that protrudes toward the other side edge 22b are alternatively repeatedly provided. Further, the wavy-shaped first emboss 24 is formed such that a single emboss line extends in the same direction of the longitudinal direction of the groove, without crossing or being connected. Thus, a closed area surrounded by an emboss line is not provided at the bottom surface of the concave groove 22.

It is preferable that the wavy-shaped first emboss 24 is formed at the entire width of the concave groove 22. This means that the first emboss 24 is provided such that apex portions of the protruding portions 24a and 24b match or are in the vicinity of the side edges 22a and 22b of the concave groove 22, respectively. With this, the entire width of the concave groove 22 can be reinforced, and collapse of the concave groove 22 due to pressure from both sides in the width direction can be surely prevented. The above described "in the vicinity" means that the apex portions of the protruding portions 24a and 24b are provided inside the side edges 22a and 22b of the concave groove 22, respectively, within a range that is less than or equal to 2 mm, preferably, less than or equal to 1 mm.

As illustrated in FIG. 6, it is preferable that the wavy-shaped first emboss 24 is formed by a curved line that bulges outward in the width direction with radius. With this, the collapse due to the pressure from outsides can be surely prevented. It is preferable that the wavy-shaped first emboss 24 is formed in a sine wave shape, in total, however, may be formed by a pattern in which a semicircular ark is alternately reversely repeatedly provided.

The distance T (a period of the wavy-shaped first emboss 24) between two adjacent protruding portions 24a of the wavy-shaped first emboss 24 at the same side may be 16 mm to 25 mm, preferably, may be 18 mm to 22 mm. With this, the concave groove 22 can be surely reinforced, wrinkles, twists and splits of the front surface material can be prevented and runnability is improved. The wavy-shaped first emboss 24 is formed to have substantially the same distance T for the entire length of the concave groove 22 (formed at substantially the same period).

Meanwhile, the second emboss 25 is a plurality of embosses each of which is formed as a continuous line along the longitudinal direction of the concave groove 22 at a predetermined range. The second emboss 25 is formed along the concave groove 22 means that a straight line connecting end portions of each of the embosses substantially extends along the longitudinal direction of the concave groove 22, and includes, in addition to a case in which the straight line is parallel to the longitudinal direction of the groove line, a case in which the straight line has an angle difference with respect to the longitudinal direction of the groove line within about ±20°. Further, the line extending along the longitudinal direction is not necessarily a straight line, and may be formed by a curved line, a polygonal line, a wavy line or the like.

The second emboss 25 is formed at side edge portions of the concave groove 22, that are opposite of protruding portions 24a and 24b of the wavy-shaped first emboss 24 that protrude outwardly in the width direction, respectively. This means that at the protruding portion 24a that protrudes toward the one side edge 22a of the concave groove 22, the second emboss 25 is formed along the opposing other side edge 22b, and at the protruding portion 24b that protrudes toward the other side edge 22b of the concave groove 22, the second emboss 25 is formed along the opposing one side edge 22a.

The second emboss 25 is provided such that an edge portion at the outer side matches the side edge 22a or 22b of the concave groove 22, or in the vicinity of the side edge 22a or 22b of the concave groove 22. In the vicinity means that the edge portion of the second emboss 25 at the outer side is provided at inside the side edges 22a and 22b of the concave groove 22 within a range that is less than or equal to 2 mm, preferably, less than or equal to 1 mm. With this, similar to the wavy-shaped first emboss 24, the concave groove 22 can be reinforced for a large range in the width direction.

By providing the wavy-shaped first emboss 24 to reciprocate between the both side edges 22a and 22b of the concave groove 22, and providing the second emboss 25 at side edge portions 22a and 22b of the concave groove 22, the first emboss 24 and the second emboss 25 are provided to overlap in the longitudinal direction of the groove. With this, the wavy-shaped first emboss 24 and the second emboss 25 are provided to have resistance forces against pressure of legs from outside in the width direction at the same position in the width direction of the groove.

It is preferable that the second emboss 25 is formed by a straight line extending along the longitudinal direction of the concave groove 22 within a predetermined range at which the wavy-shaped first emboss 24 becomes a concave portion. With this, as the second emboss 25 is provided along the side edge of the concave groove 22, a broader range of reinforcement can be obtained against the pressure from outside at the side where the second emboss 25 is provided.

The second emboss 25 is provided at a position in the width direction of the groove such that its center portion in the longitudinal direction of the groove matches an apex portion of each of the protruding portions 24a and 24b of the wavy-shaped first emboss 24. This means that if a groove width direction line is drawn at the apex portion of each of the protruding portions 24a and 24b of the wavy-shaped first emboss 24, the second emboss 25 is formed to have the same lengths in the longitudinal direction of the groove at both sides of the groove width direction line as a center.

Further, the wavy-shaped first emboss 24 and the second emboss 25 are formed not to be connected with each other and to be apart from each other such that the emboss lines are independent from each other in the incontinence pad 1. Thus, the highly compressed portion 23 is formed by a single continuous first emboss 24 that extend along the concave groove 22, and the second emboss 25 is provided at each of the concave portions of the wavy-shaped first emboss 24. This means that a plurality of the second embosses 25 are provided at predetermined positions, apart from each other, in the concave groove 22.

As illustrated in FIG. 6, it is preferable that the distance width "C" between the wavy-shaped first emboss 24 and the second emboss 25, at which a straight line between both embosses becomes the shortest, is greater than or equal to 2 mm and less than or equal to 5 mm (2 mm≤C≤5 mm). If this distance width "C" is less than 2 mm, the pressure in emboss compression is difficult to be dispersed, and wrinkles and the like are easily generated and an emboss roller is easily blocked because paper powders enter space portions. On the other hand, if the distance width "C" is greater than 5 mm, the concave portion of the wavy-shaped first emboss 24 are not sufficiently reinforced and the concave groove 22 is easily collapsed.

Figure 7:
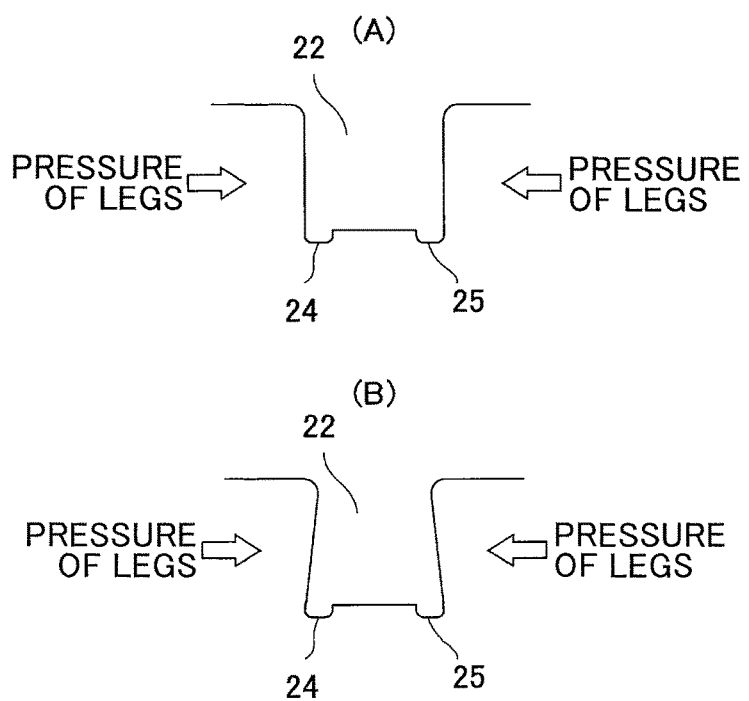
FIG. 7-(A) is a cross-sectional view of FIG. 6 taken along a VII-VII line before the concave groove 22 is deformed, and FIG. 7-(B) is a cross-sectional view of FIG. 6 taken along a VII-VII line after the concave groove 22 is deformed.
Figure 11:
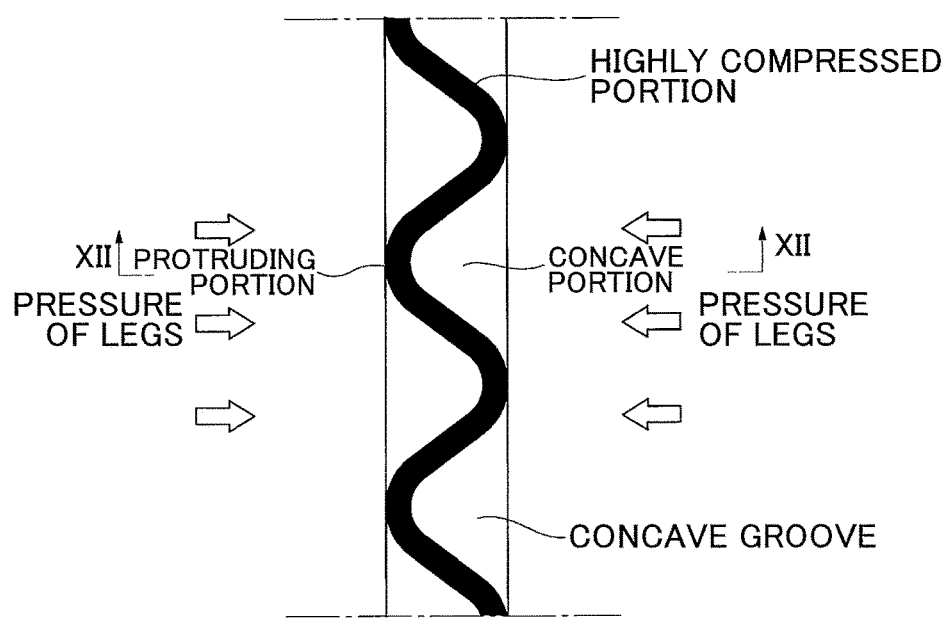
FIG. 11 is an enlarged plan view of a concave groove in which only a first emboss 24 is provided.
Figure 12:
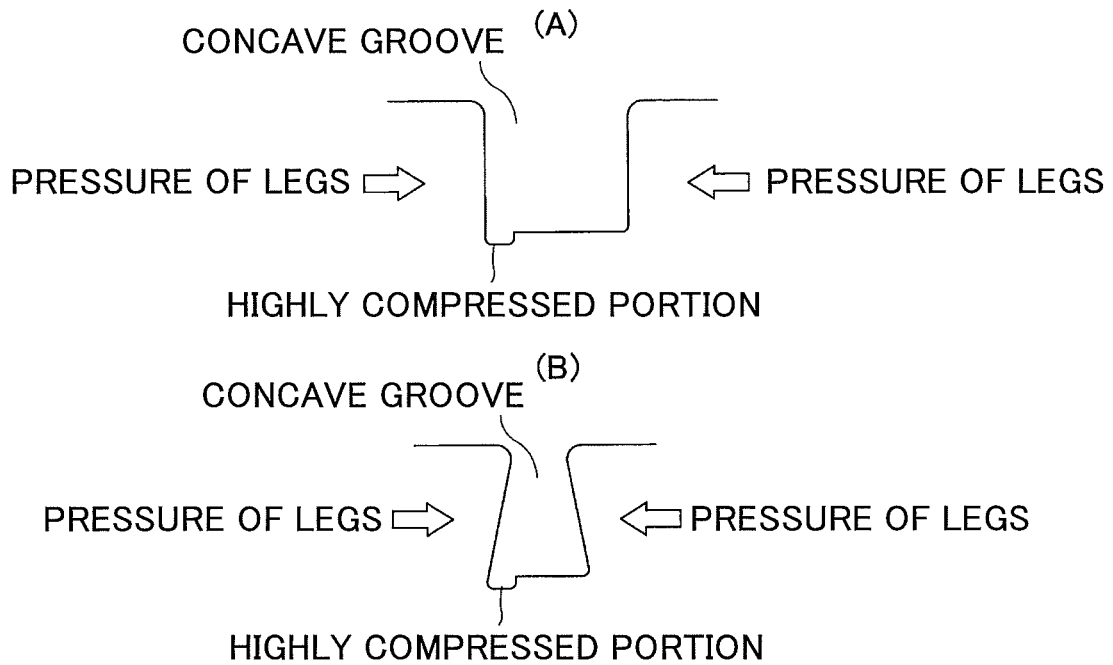
FIG. 12-(A) is a cross-sectional view of FIG. 11 taken along a XII-XII line before the concave groove is deformed, and FIG. 12-(B) is a cross-sectional view of FIG. 11 taken along a XII-XII line after the concave groove is deformed.

As described above in detail, the highly compressed portion 23 constituted by the wavy-shaped first emboss 24 and the second emboss 25 is formed at the bottom surface of the concave groove 22 in the incontinence pad 1. If the highly compressed portion is constituted by only the wavy-shaped first emboss 24, as illustrated in FIG. 11 and FIG. 12, resistance force against pressure of legs from outside in the width direction becomes weak at a concave portion at which the wavy-shaped emboss is not formed. Thus, the concave groove collapses to reduce the reserving volume of the urine of the concave groove and the urine is difficult to be absorbed in the absorbent body. On the other hand, according to the incontinence pad 1, as illustrated in FIG. 7, the second emboss 25 is provided at a portion corresponding to the concave portion of the wavy-shaped first emboss 24. Thus, resistance force become large against pressure of legs from both side in the width direction, and the concave groove 22 is hardly collapsed.

Further, the wavy-shaped first emboss 24 and the second emboss 25 are not connected with each other in the incontinence pad 1, and each of the emboss lines are independently formed to be apart from each other. Thus, no area is formed at the bottom surface of the concave groove 22 that is surrounded by the continuous highly compressed portion 23. Therefore, portions between the embosses function as escapeways for compression force when embossing to disperse the pressure. Thus, distortion of the front surface material by the compression is not accumulated, splits of the front surface material, blocking of the emboss roller and the like are not generated, and runnability is improved.

Here, it is preferable that the fabric weight per unit area of the superabsorbent polymer 8 provided at the bottom of the absorbent body concave portion 20 of the absorbent body 4 is smaller than that at other areas in the incontinence pad 1 in order to prevent splits of the front surface material when forming the highly compressed portion 23. If a large amount of the superabsorbent polymer 8 is provided at this area, splits are easily generated in the front surface material due to the superabsorbent polymer 8. Thus, by reducing the amount of polymer, risk of generation of splits in embossing is reduced.

Figure 8:
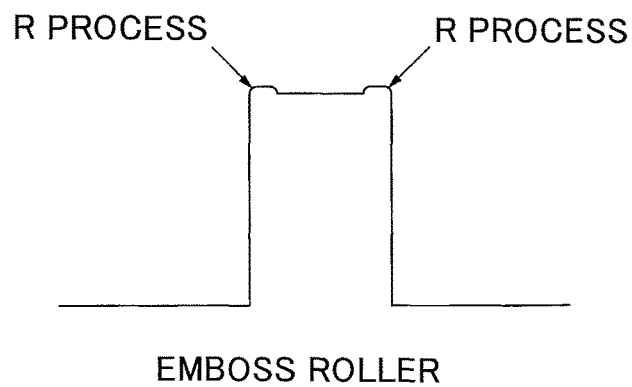
FIG. 8 is a cross-sectional view illustrating emboss protruding portions of an emboss roller.

Further, when providing the highly compressed portion 23, the emboss roller provided with an emboss protruding portion of a predetermined pattern is used. As illustrated in FIG. 8, it is preferable that an R process (R chamfering) is performed at corner portions at a front end of the emboss protruding portion of the emboss roller. With this, compared with corner portions at which the R process is not performed, or corner portions at which a C process of chamfering is performed, splits of the liquid permeable topsheet 3 can be surely prevented.

Further, groove widths and depths of the wavy-shaped first emboss 24 and the second emboss 25 may be different, however, it is preferable that they are the same so that uniform resistance forces are generated against pressures from both sides in the width direction.

Figure 13:
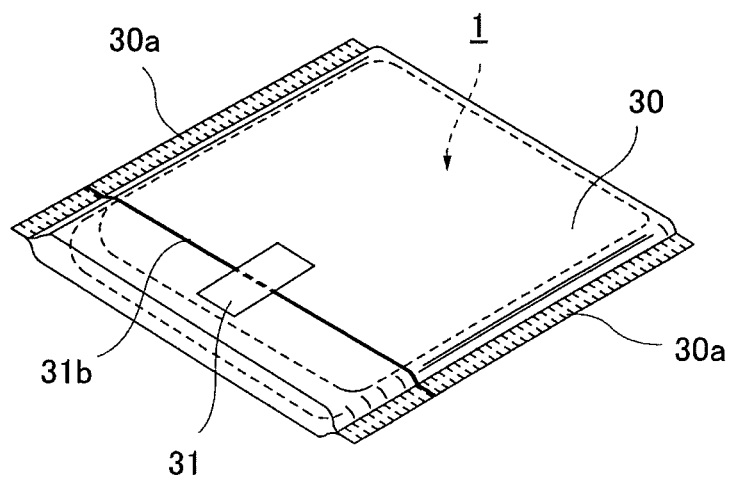
FIG. 13 is a perspective view illustrating the incontinence pad 1 in an item packaging.

Here, the incontinence pad 1 is item packaged, after placed on an item packaging sheet 24, by being appropriately folded in the longitudinal direction (see FIG. 13). Specifically, as illustrated in FIG. 1, after placing the incontinence pad 1 on the item packaging sheet 24, the incontinence pad 1 is item packaged by folding a pad rear end portion toward a liquid permeable topsheet 3 side with the item packaging sheet 30 at a rear bend line L1, folding a pad front end portion toward the liquid permeable topsheet 3 side with the item packaging sheet 30 at a front bend line L2, and thereafter, as illustrated in FIG. 13, sealing side edge portions 30a of the item packaging sheet 30, that are open, by one of or a combination of sealing means such as emboss sealing, heat fusion, an adhesive agent and the like. Further, after bonded by the adhesive agent, preferably, front and rear end edges 30b of the item packaging sheet 24 are sealed by a tag tape 31.

Figure 14:
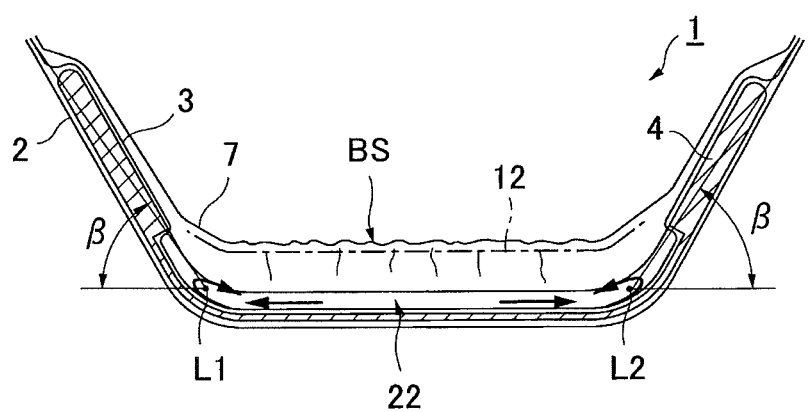
FIG. 14 is a longitudinal cross-sectional view illustrating a status of the incontinence pad 1 that is taken out from the item packaging.

As illustrated in FIG. 14, after taking out from the item packaging, a rear side and a front side of the incontinence pad 1 with respect to the bend line L1 and the bend line L2, respectively, stand toward the skin side. "Taking out from the item packaging" means a natural status of the incontinence pad 1 for which the item packaging sheet 30 is removed after the item packaging is opened (if a releasing paper is provided that covers the slip stopper adhesive layer that is provided at an outer surface of the liquid impermeable backsheet 2, the releasing paper is removed as well). "A rear side and a front side of the incontinence pad 1 stand toward the skin side" means that the front end and the rear end of the incontinence pad 1 stand toward the skin side (liquid permeable topsheet 3 side) from the bend lines L1 and L2, respectively. At this time, as illustrated in FIG. 14, it is preferable that the standing angle is such that an angle "β" between a line connecting the folded position and the front end or the rear end of the pad, and a horizontal line is 45° to 180°.

The reason that the rear side and the front side stand toward the skin side from the bend line L1 and the bend line L2, respectively, may be a case due to creases formed when the incontinence pad 1 is folded at the bend lines L1 and L2 in item packaging, a case due to retraction force of the elastic stretchable members 12 and 13 that constitute the standing gathers BS provided at the both side portions of the incontinence pad 1, or due to both of them.

As illustrated in FIG. 1, the concave groove 22 is provided such that the front end 22*a* in the longitudinal direction extends toward the front side of the incontinence pad 1 with respect to the front bend line L2, and the rear end 22*b* in the longitudinal direction extends toward the rear side of the incontinence pad 1 with respect to the rear bend line L1. This means that the concave groove 22 is continuously provided between the front and rear bend lines L1 and L2 including the urine expelling area H to areas at the rear side and the front side that exceed the bend lines L1 and L2, respectively. In other words, the bend lines L1 and L2 for item packaging the incontinence pad 1 are provided at positions crossing the concave groove 22. It is preferable that the extending size (protruding length) of the concave groove 22 from the bend lines L1 and L2 is about 10 to 30 mm.

The urine flowed into the concave groove 22 flows along the longitudinal direction of the groove in the concave groove toward the end portions of the concave groove 22. However, if the front and rear end portions of the concave groove 22 are formed between the bend line L1 and the bend line L2, not exceeding the bend lines L1 and L2, the urine that is overflowed from the end portions of the concave groove 22 is suddenly blocked at the bend lines L1 and L2, respectively, because the portions that stand toward the skin side function as high walls, and the urine flows in the width direction at the bend lines L1 and L2 to cause side leak. Further, in such a case, the end portions of the concave groove 22 are often formed near the polygonal lines L1 and L2, and the absorbent body near the polygonal lines L1 and L2 is often compressed by the folding of the incontinence pad. Thus, the depth of the end portions of the concave groove may be shallow and the urine is easily overflowed from the concave groove.

On the other hand, according to the incontinence pad 1, as described above, the rear and front sides with respect to the bend lines L1 and L2, respectively, stand toward the skin side, and the front end and the rear end of the concave groove 22 are provided to extend toward the end portions with respect to the bend lines L1 and L2. Thus, as illustrated in FIG. 14, the portion that stands toward the skin side becomes a high wall and functions as a parapet for the urine that flows in the concave groove 22 toward the end portion (the urine flows in an opposite direction by a reaction of collision against the standing portion, that becomes the wall), the urine does not overflow from the concave groove 22, and the urine is accumulated in the concave groove 22 to be gradually absorbed and retained in the absorbent body. Thus, the urine in the concave groove 22 is prevented from overflowing from the concave groove 22 to leak from sides at the bend lines L1 and L2.

Here, only the front end 22*a* of the concave groove 22 may extend toward a front side with respect to the front bend line L2, or only the rear end 22*b* of the concave groove 22 may extend toward a rear side with respect to the rear bend line L1. For the former case, urine is prevented from flowing out from the front end 22*a* of the concave groove 22, and for the latter case, urine is prevented from flowing out from the rear end 22*b* of the concave groove 22.

Figure 15:
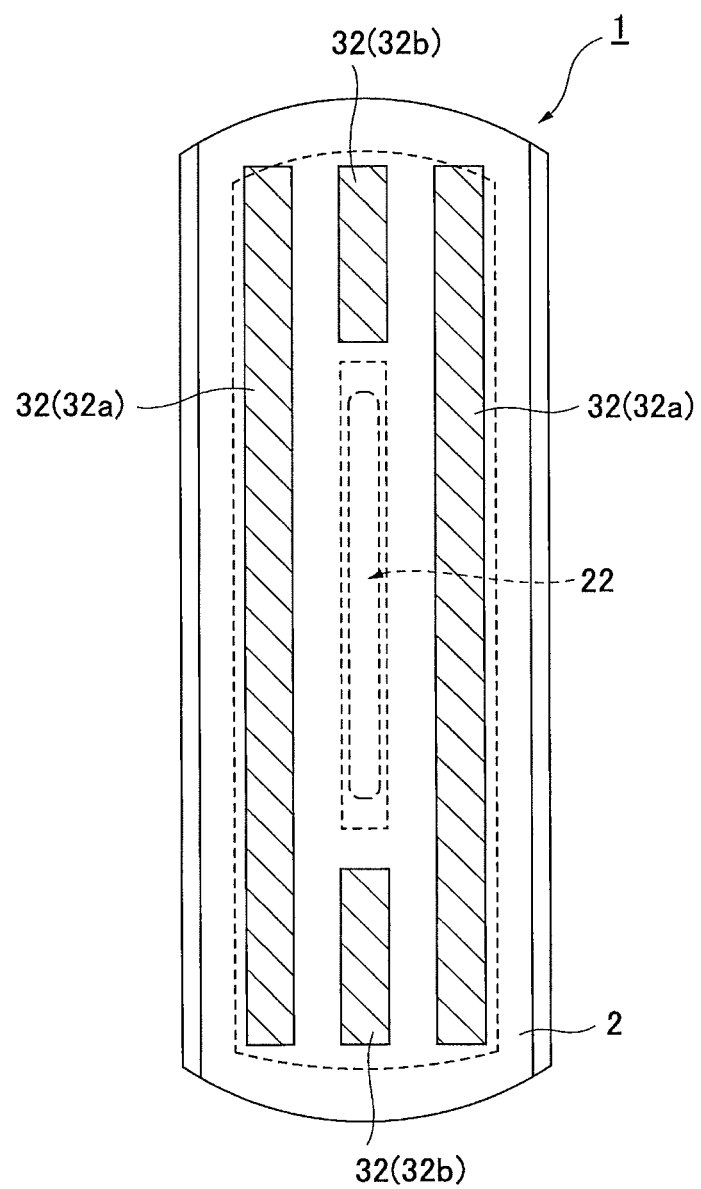
FIG. 15 is a back view of the incontinence pad 1.

Here, as illustrated in FIG. 15, the slip stopper adhesive layer 25 is provided at the outer surface of the liquid impermeable backsheet 2 of the incontinence pad 1 for stopping slip between an underwear when being worn. It is preferable that the slip stopper adhesive layer 32 is not provided at a range that overlaps the concave groove 22 in a thickness direction. With this, even when the concave groove 22 is collapsed in the width direction due to pressure of legs from both sides in the width direction when being worn, a space is formed and the slip stopper adhesive layer 25 is prevented from being adhered with each other, and the concave groove 22 can return to its original shape when the pressure of legs is removed.

For the example illustrated in FIG. 15, the slip stopper adhesive layer 25 includes band-like slip stopper adhesive layers 32*a* provided at both sides, apart from each other, that are outward of the concave groove 22 in the width direction, and at substantially entire length of a portion at which the absorbent body 4 exists along the longitudinal direction of the pad, and band-like slip stopper adhesive layers 32*b* provided at front and rear end portions, apart from each other, that are outward of the end portions of the concave groove 22, along the longitudinal direction of the pad to extend toward the end portions of the absorbent body 4. Here, at least the slip stopper adhesive layers 32*a* at both sides of the concave groove 22 are provided, the slip stopper adhesive layers 32*b* at the front and rear end portions of the concave groove 22 may not be provided.

Figure 16:
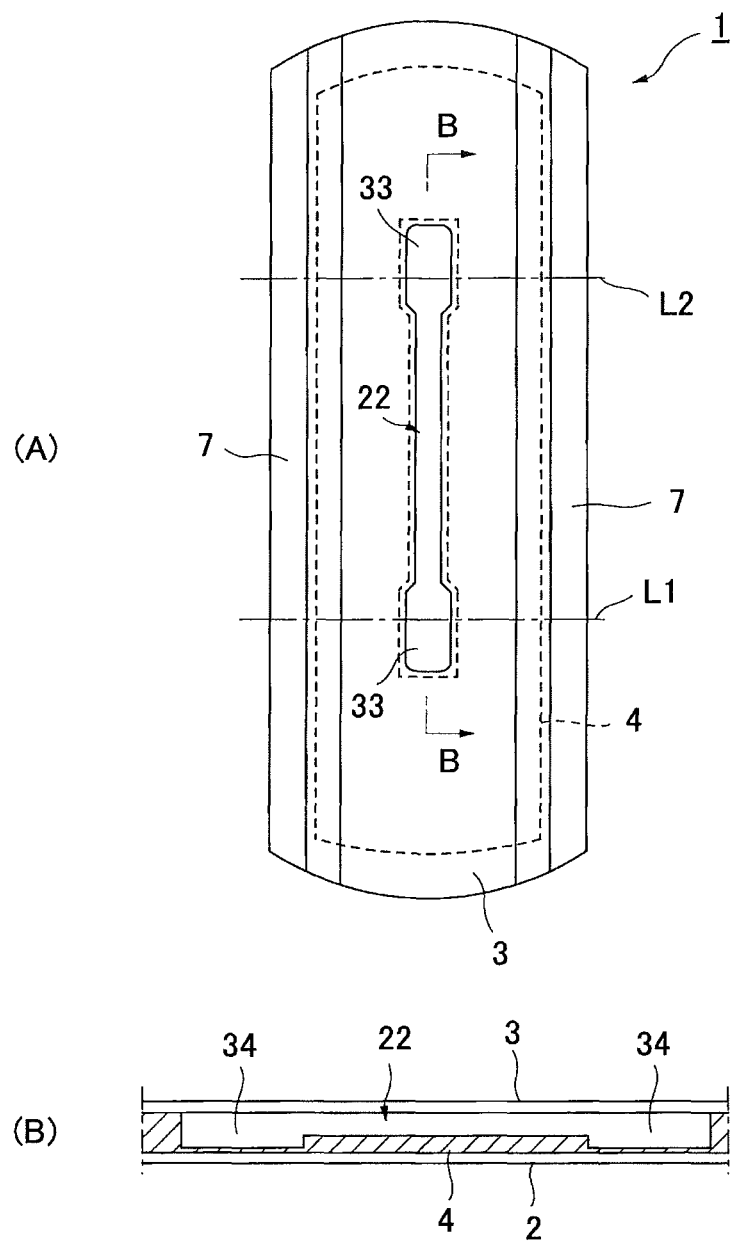
FIG. 16-(A) is a plan view of the incontinence pad 1, and FIG. 16-(B) is a cross-sectional view of FIG. 16-(A) taken along a B-B line.

According to the incontinence pad 1, as the end portions of the concave groove 22 extend outward with respect to the bend lines L1 and L2, respectively, there is a risk that, when the urine that flows along the concave groove 22 strongly collides against the wall portions standing toward the skin side, the urine overflows from both sides of the concave groove 22, diffuses both sides along the bend lines and side leak occurs. In order to solve such a problem, as illustrated in FIG. 16, it is preferable that the concave groove 22 is provided with wide width portions 33 whose groove width is enlarged, and deep depth portions 34 whose groove depth is increased at end portions that extend outward with respect to the bend lines L1 and L2. Further, it is preferable that each of the wide width portions 33 and the deep depth portions 34 is formed to extend from a center side of the bend lines L1 and L2 to the end portion in the longitudinal direction of the pad, respectively. By providing the wide width portions 33 and the deep depth portions 34, flowing speed of the urine that flows along the concave groove 22 is lowered due to the increasing of the cross-sectional dimension right before colliding against the wall portion that stands toward the skin side. Thus, the strength to collide against the standing wall portion is weakened and the urine does not overpass the concave groove 22, and the effect of preventing overflow of the urine by the parapet can be surely obtained. Further, as the dimension around the concave groove 22 increases at the wide width portion 33 and the deep depth portion 34, absorbing dimension of the urine is increased and absorbing ability for the urine is improved. Here, although both of the wide width portion 29 and the deep depth portion 30 are formed at the end portion of the concave groove 22 in the illustrated example, one of the wide width portion 33 and the deep depth portion 34 may be provided.

Figure 17:
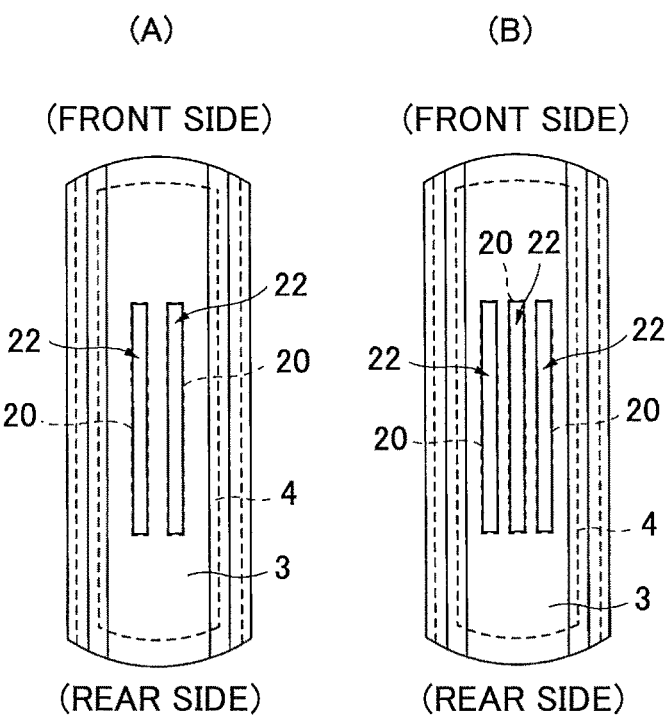
FIG. 17-(A) and FIG. 17-(B) are developed views of the incontinence pad 1 illustrating other examples of the concave groove 22.

The concave groove 22 may be placed in various embodiments. As illustrated in FIG. 1, it is preferable that only the single concave groove 22 is formed at a middle portion in the pad width direction corresponding to the urine expelling area H and at an intermediate portion in the longitudinal direction. However, as illustrated in FIG. 17-(A) and FIG. 17-(B), a plurality of the concave grooves 22 may be formed with spaces therebetween in the width direction of the pad. If the plurality of the concave grooves 22 are formed, a diffusing effect of the urine can be reliably increased even when a large amount of urine is expelled at once. Further, if the concave groove 22 is formed as a discontinuous line, the concave groove 22 can be surely prevented from being collapsed even when pressure of legs or the like is applied from both sides in the width direction. When the plurality of the concave grooves 22 are formed with the spaces therebetween in the width direction of the pad, the number of the concave grooves 22 may be even as illustrated in FIG. 17-(A), or may be odd as illustrated in FIG. 17-(B).

Figure 18:
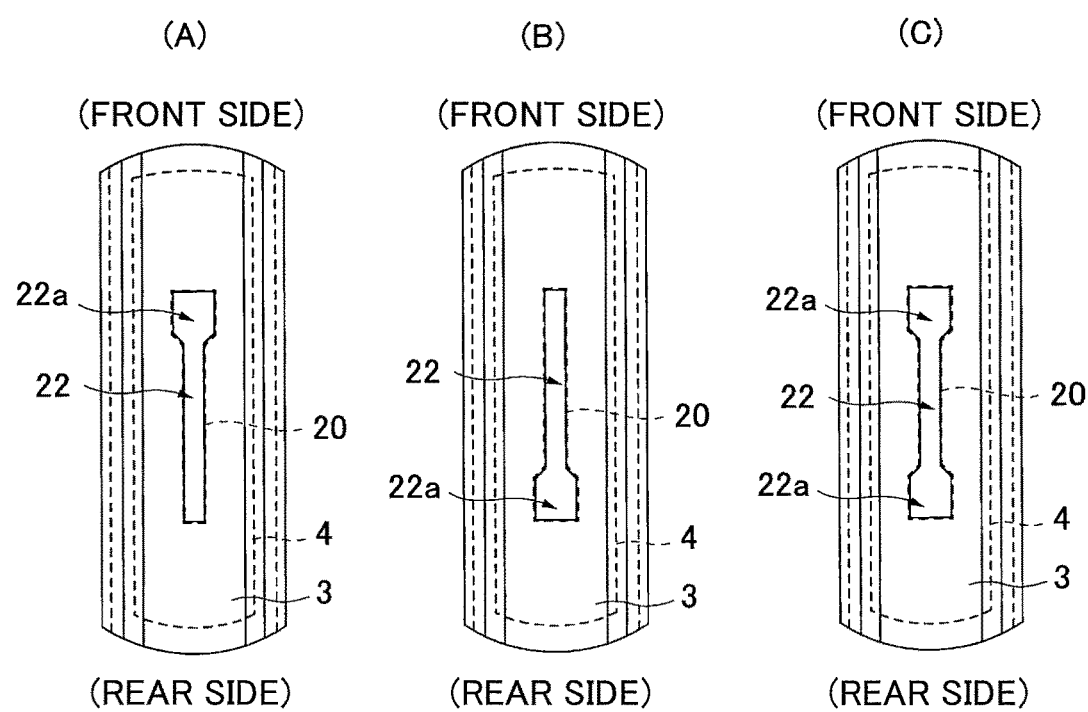
FIG. 18-(A) to FIG. 18-(C) are developed views of the incontinence pad 1 illustrating other examples of the concave groove 22.

Further, as illustrated in FIG. 1, the concave groove 22 may be formed to have a planar shape whose width is the same in the longitudinal direction of the pad, or as illustrated in FIG. 18, the concave groove 22 may be formed to have a planar shape whose groove width is different. In FIG. 18-(A), a wide width portion 22a whose groove width is enlarged is provided at a front end portion of the concave groove 22 in the longitudinal direction of the pad. By providing the wide width portion 22a, a space for temporarily reserving the urine can be enlarged, and the urine can be surely received in the concave groove 22 even when a large amount of urine is expelled at once, in particular, such as urinary urge incontinence. As illustrated in FIG. 18-(B), the wide width portion 22a may be provided at a rear end portion of the pad, or as illustrated in FIG. 18-(C), the wide width portions 22a may be provided at front and rear end portions, respectively.

Figure 19:
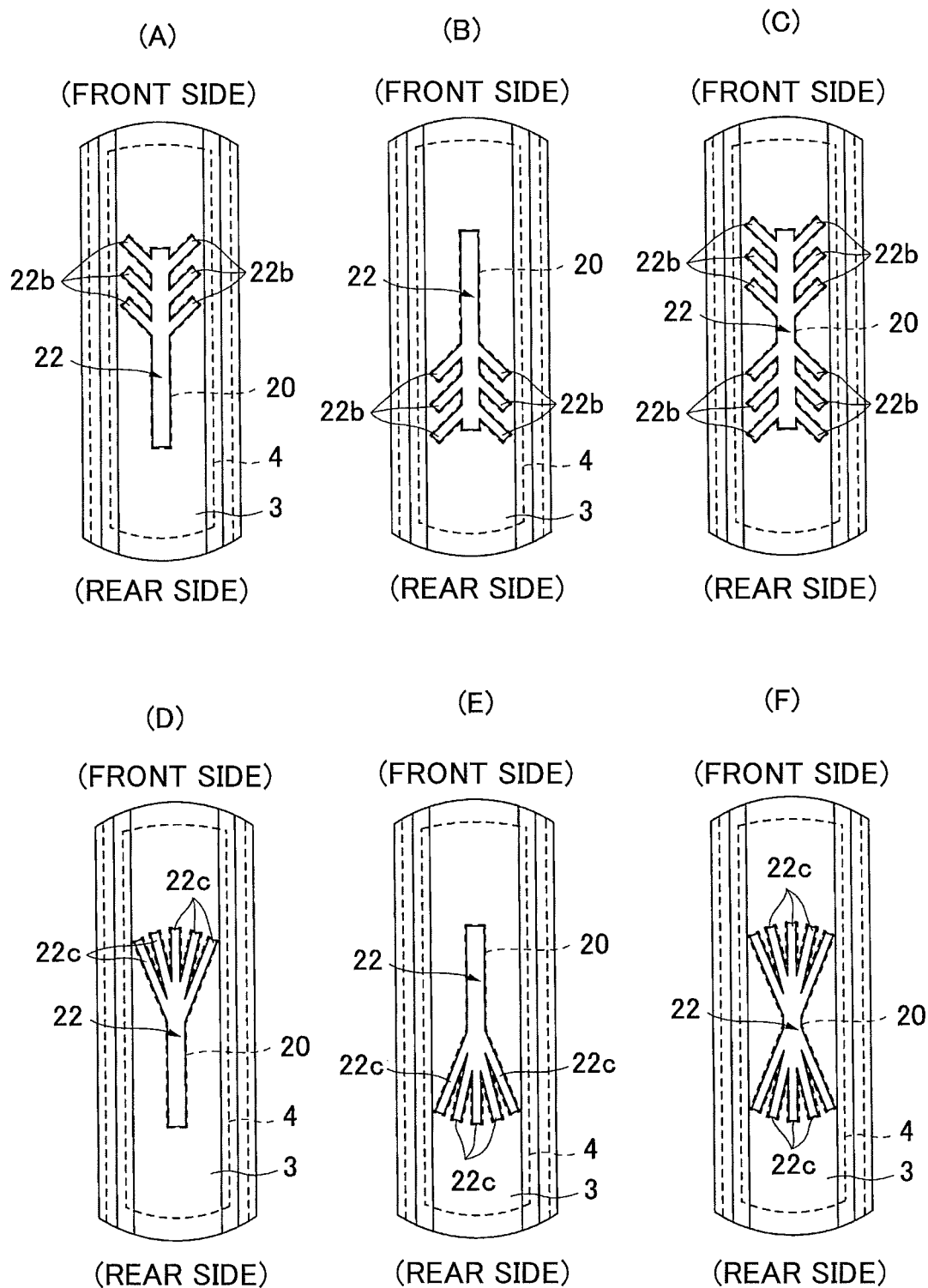
FIG. 19-(A) to FIG. 19-(F) are developed views of the incontinence pad 1 illustrating other examples of the concave groove 22.

As illustrated in FIG. 19, the concave groove 22 may be provided with one or a plurality of branch portions 22b and 22c. By providing the branch portions 22b and 22c, the urine temporarily reserved in the concave groove 22 can diffuse in a wide range of the absorbent body 4 along the concave groove 22 and the urine can be absorbed in the wider range of the absorbent body 4. For the examples illustrated in FIG. 19-(A) to FIG. 19-(C), a plurality of the branch portions 22b, three at both sides for the example illustrated in the drawings, that extend outwardly from both side edges of the concave groove 22 to be inclined toward an end portion in the longitudinal direction of the pad are provided at a front side, a rear side or front and rear sides, respectively, in the longitudinal direction of the pad. Further, for the examples illustrated in FIG. 19-(D) to FIG. 19-(F), a plurality of the branch portions 22c radially branched from the concave groove 22, branched into five for the example illustrated in the drawings, are provided at a front end, a rear end or front and rear ends, respectively, in the longitudinal direction of the pad.

Here, when previously providing the absorbent body concave portion 20 at a portion of the absorbent body 4 for the concave groove 22, the absorbent body concave portion 20 is provided in accordance with the shape of the concave groove 22.

(Other Embodiments)

Figure 9:
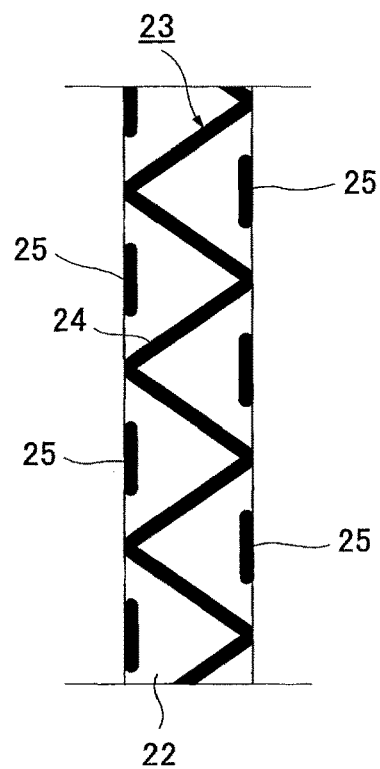
FIG. 9 is an enlarged plan view of the concave groove 22 of another example.

(1) As long as the wavy-shaped first emboss 24 is formed by a pattern in which the unit section 26, obtained by sectioning the he concave groove 22 in the longitudinal direction, is repeatedly positively inverted in the longitudinal direction of the groove, the wavy-shaped first emboss 24 being formed by extending in the width direction of the groove while inclining in the longitudinal direction of the groove to cross from a side end at one side to a side end at the other side of the concave groove 22 in the unit section 26, as illustrated in FIG. 9, each of the protruding portions 24a and 24b that protrude outwardly in the width direction may be formed in a triangle shape, a trapezoidal shape, or a square shape.

Figure 10:
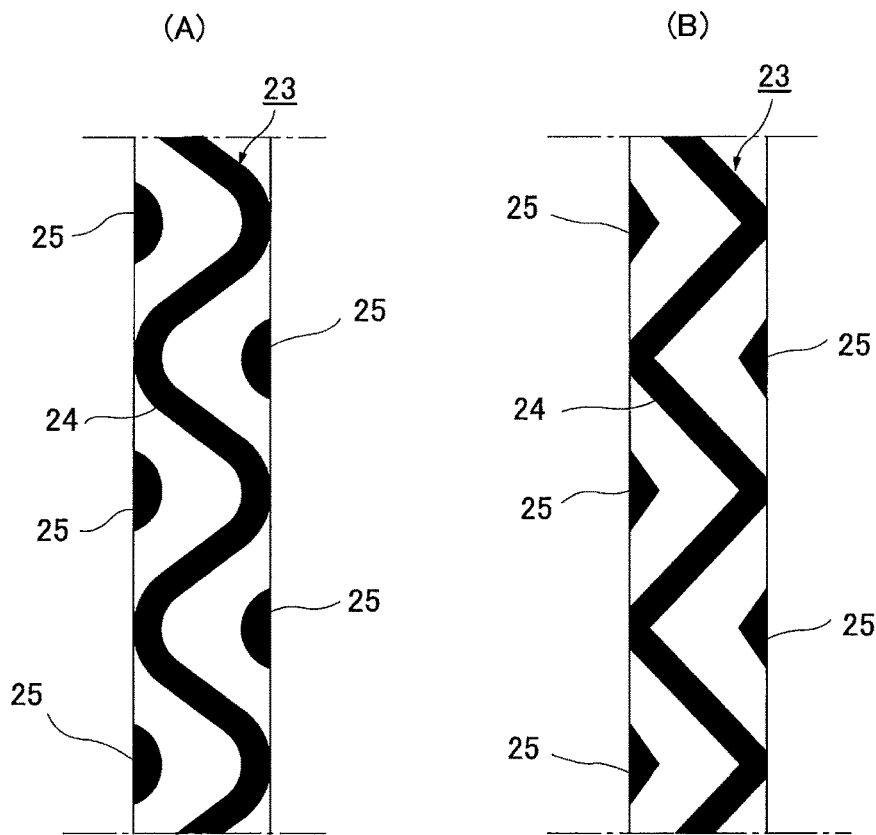
FIG. 10 is an enlarged plan view of the concave groove 22 of other examples.

(2) As long as the second emboss 25 is formed along the concave groove 22, as illustrated in FIG. 10, the second emboss 25 may be formed by a plane pattern whose plane shape is (A) a semicircle shape, (B) a triangle shape or the like. Further, as illustrated in FIG. 10-(A), when the wavy-shaped first emboss 24 is formed by a curved line, it is preferable that the second emboss 25 is formed to have a semicircle shape whose outline of the emboss is a curved line corresponding to the curved line of the wavy-shaped first emboss 24. As illustrated in FIG. 10-(B), when the wavy-shaped first emboss 24 is formed by a zig-zag line, which is a straight line, it is preferable that the second emboss 25 is formed to have a triangle patter whose outline of the emboss is a straight line corresponding to the zig-zag line of the wavy-shaped first emboss 24.

NUMERALS

1 . . . incontinence pad, 2 . . . liquid impermeable backsheet, 3 . . . liquid permeable topsheet, 4 . . . absorbent body, 7 . . . side non-woven fabric, 8 . . . superabsorbent polymer, 10 . . . inner standing gather, 11 . . . outer standing gather, 12, 13 . . . threadlike elastic stretchable member, 20 . . . absorbent body concave portion, 21 . . . emboss portion, 22 . . . concave groove, 23 . . . highly compressed portion, 24 . . . first emboss, 25 . . . second emboss, 26 . . . unit section, 30 . . . item packaging sheet, 31 . . . tag tape, 32 . . . slip stopper adhesive layer, 33 . . . wide width portion, 34 . . . deep depth portion

What is claimed is:

1. An absorbent article comprising:
   an absorbent body provided between a liquid permeable topsheet and a backsheet; and
   at least a single concave groove for flowing urine therein formed at a skin side surface along a longitudinal direction,
   wherein a transverse plane shape of the concave groove satisfies following conditional expressions (1), (2) and (3),
   (1) a relationship between a depth "h" of a bottom surface of the concave groove, and a distance "S" from a bottom end "G" of the concave groove to an upper end "K" from which a concavity of the concave groove starts is 1.5h<S.
   (2) a relationship between a width "b" of the bottom surface of the concave groove, and a width "B" of a liquid collection area expressed by a distance between the upper ends "K" and "K" at both sides of the concave groove is B≥3b, and
   (3) a relationship between a dimension "a" of a square concave groove expressed by a product of the width "b" of the bottom surface of the concave groove and the depth "h" of the bottom surface, and a cross-sectional dimension "A" of the concave groove is A≥2a, and
   wherein in the concave groove, a density "ρ1" of the absorbent body under the bottom surface is greater than or equal to 1.5 times of a density "ρ2" of the absorbent body at a peripheral general portion which is not compressed.

2. The absorbent article according to claim 1,
   wherein the absorbent body is provided with an absorbent body concave portion formed at a surface at a liquid permeable topsheet side along a longitudinal direction of the absorbent body over a range including an urine expelling area in the longitudinal direction, without compression, and the concave groove is formed by embossing from a front surface side of the liquid permeable topsheet, under a status that the liquid permeable topsheet is stacked, to a bottom surface of the absorbent body concave portion, and
   wherein, before embossing, a fabric weight per unit area "β1" of the absorbent body under the bottom surface of the concave groove is less than or equal to 55% of a fabric weight per unit area "β2" of the absorbent body at the peripheral general portion which is not compressed.

3. The absorbent article according to claim 1, further comprising standing gathers at both side portions at a skin surface side,
wherein the width "B" of the liquid collection area is greater than or equal to ⅓ of an inside size "W" of standing ends of the standing gathers.

4. The absorbent article according to claim 1, wherein a length of the concave groove in a longitudinal direction is 100 to 180 mm, and the width "b" of the bottom surface of the concave groove is 5 to 30 mm.

5. The absorbent article according to claim 1, wherein the absorbent article is folded in three in a longitudinal direction by front and rear bend lines, and a front side and a rear side with respect to the front and rear bend lines, respectively, stand toward a skin side when the absorbent article is taken out from an item packaging, and
wherein a from end of the concave groove extends toward the front side of the front bend line, a rear end of the concave groove extends toward the rear side of the rear bend or the front end of the concave groove extends toward the front side of the front bend line and the rear end of the concave groove extends toward the rear side of the rear bend line.

6. The absorbent article according to claim 5, wherein a fabric weight per unit area of pulp of the absorbent body at a portion other than the concave groove is greater than or equal to 400 g/m$^2$, and
wherein a ratio, with respect to a weight of the absorbent body, which is a total of a weight of entire pulp and a weight of entire polymer, of the weight of the entire pulp is greater than or equal to 55%.

7. The absorbent article according to claim 5. further comprising a slip stopper adhesive layer provided at an outer surface side of the backsheet, and
wherein the slip stopper adhesive layer is not provided at a range that overlaps the concave groove in a thickness direction.

8. The absorbent article according to claim 5, wherein the concave groove is provided with one of or both of a wide width portion whose groove width is enlarged and a deep depth portion whose groove depth is increased at an end portion that extends outward with respect to the bend line, and the wide width portion or the deep depth portion is formed from a center side position to the end portion with respect to the bend line.

* * * * *